US009291598B2

(12) United States Patent
(10) Patent No.: US 9,291,598 B2
(45) Date of Patent: Mar. 22, 2016

Sakai et al.

(54) BIOLOGICAL INFORMATION ACQUIRING SYSTEM INCLUDING A BIOLOGICAL INFORMATION ACQUIRING APPARATUS HAVING A BIOLOGICAL INFORMATION ACQUIRING SECTION AND A MAGNETIC FIELD GENERATION SECTION, AND METHOD OF DRIVING THE BIOLOGICAL INFORMATION ACQUIRING SYSTEM

(71) Applicant: OLYMPUS CORPORATION, Tokyo (JP)

(72) Inventors: Youhei Sakai, Ina (JP); Naoki Yoshida, Tachikawa (JP); Fukashi Yoshizawa, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 167 days.

(21) Appl. No.: 14/165,866

(22) Filed: Jan. 28, 2014

(65) Prior Publication Data

US 2014/0139212 A1 May 22, 2014

Related U.S. Application Data

(63) Continuation of application No. PCT/JP2012/064108, filed on May 31, 2012.

(30) Foreign Application Priority Data

Jul. 28, 2011 (JP) ................................ 2011-165808

(51) Int. Cl.
*G01N 27/72* (2006.01)
*A61B 1/00* (2006.01)
(Continued)

(52) U.S. Cl.
CPC ............ *G01N 27/72* (2013.01); *A61B 1/00036* (2013.01); *A61B 5/073* (2013.01); *A61B 1/041* (2013.01)

(58) Field of Classification Search
CPC .... A61B 1/00036; A61B 1/041; A61B 5/073; G01N 27/72
USPC ............... 324/207.15–207.17, 244, 260, 257; 600/117, 118, 12, 431, 407
See application file for complete search history.

(56) References Cited

U.S. PATENT DOCUMENTS

2005/0049488 A1 3/2005 Homan
2009/0275801 A1 11/2009 Sakai
(Continued)

FOREIGN PATENT DOCUMENTS

EP 1 875 852 A1 1/2008
JP 2005-081005 A 3/2005
(Continued)

OTHER PUBLICATIONS

International Search Report dated Aug. 7, 2012 issued in PCT/JP2012/064108.
(Continued)

*Primary Examiner* — Jay Patidar
(74) *Attorney, Agent, or Firm* — Scully, Scott, Murphy & Presser, P.C.

(57) ABSTRACT

A biological information acquiring system includes a biological information acquiring apparatus having a biological information acquiring section, and a magnetic field generation section, and the biological information acquiring apparatus includes: a power source section which supplies power for driving the biological information acquiring section; a magnetic field detection section which outputs a magnetic field detection signal according to a detection result of a magnetic field generated from the magnetic field generation section; a first switching control section which performs control an on/off state of a first switch section connected to the power source section based on an output state of the magnetic field detection signal; and a second switching control section which performs control the on/off state of a second switch section connected between the first switch section and the biological information acquiring section, based on the output state of the magnetic field detection signal.

11 Claims, 13 Drawing Sheets

(51) Int. Cl.
*A61B 5/07* (2006.01)
*A61B 1/04* (2006.01)

(56) References Cited

U.S. PATENT DOCUMENTS

| | | | | |
|---|---|---|---|---|
| 2009/0299142 | A1* | 12/2009 | Uchiyama .......... | A61B 1/00158 600/118 |
| 2012/0095290 | A1* | 4/2012 | Kawano ............. | A61B 1/00181 600/117 |

FOREIGN PATENT DOCUMENTS

| | | | |
|---|---|---|---|
| JP | 2010-104518 | A | 5/2010 |
| JP | 2011-130840 | A | 7/2011 |

OTHER PUBLICATIONS

Extended Supplementary European Search Report dated Feb. 24, 2015 from related European Application No. 12 81 7712.8.

* cited by examiner

BIOLOGICAL INFORMATION ACQUIRING SYSTEM INCLUDING A BIOLOGICAL INFORMATION ACQUIRING APPARATUS HAVING A BIOLOGICAL INFORMATION ACQUIRING SECTION AND A MAGNETIC FIELD GENERATION SECTION, AND METHOD OF DRIVING THE BIOLOGICAL INFORMATION ACQUIRING SYSTEM

CROSS REFERENCE TO RELATED APPLICATION

This application is a continuation application of PCT/JP2012/064108 filed on May 31, 2012 and claims benefit of Japanese Application No. 2011-165808 filed in Japan on Jul. 28, 2011, the entire contents of each of which are incorporated herein by their reference.

BACKGROUND OF THE INVENTION

1. Field of the Invention

The present invention relates to a biological information acquiring system and more particularly to a biological information acquiring system capable of acquiring information inside a living body and a method of driving the biological information acquiring system.

2. Description of the Related Art

Endoscopes in medical fields have been conventionally used for observation inside a living body, or the like. As one type of the above-described endoscopes, a capsule endoscope has been proposed in recent years, and such a capsule endoscope is arranged in a body cavity by a subject swallowing the capsule, and capable of picking up an image of an object while moving inside a body cavity in accordance with a peristaltic movement and transmitting the picked-up image of the object by radio to the outside as an image pickup signal.

For example, Japanese Patent Application Laid-Open Publication No. 2010-104518 discloses a capsule endoscope having a configuration which is substantially the same as that of the above-described capsule endoscope.

Specifically, the Japanese Patent Application Laid-Open Publication No. 2010-104518 discloses a capsule endoscope which incorporates a circuit for magnetic field detection and a circuit for power source control and has a configuration in which a magnetic field applied from outside the capsule endoscope is detected by an antenna for magnetic field detection (magnetic field detection section), and the power source of the capsule endoscope is switched between ON and OFF only when a pulse signal generated according to a result of the detection is inputted into the circuit for power source control a predetermined number of times or more within a predetermined period.

SUMMARY OF THE INVENTION

A biological information acquiring system according to the present invention includes: a biological information acquiring apparatus including a biological information acquiring section which is capable of acquiring biological information inside a subject; and a magnetic field generation section configured to be able to generate a burst alternate-current magnetic field, the biological information acquiring apparatus includes: a power source section which is capable of supplying power for driving the biological information acquiring section; a magnetic field detection section which generates a magnetic field detection signal according to a detection result of the burst alternate-current magnetic field generated from the magnetic field generation section and outputs the generated magnetic field detection signal; a first switching control section which performs control so as to switch between an on state and an off state of a first switch section connected to the power source section or maintain the on state or the off state of the first switch section, based on an output state of the magnetic field detection signal; and a second switching control section which performs control so as to switch between an on state and an off state of a second switch section connected between the first switch section and the biological information acquiring section or maintain the on state or the off state of the second switch section, based on the output state of the magnetic field detection signal, when power is supplied from the power source section by the first switch being turned on.

DETAILED DESCRIPTION OF THE PREFERRED EMBODIMENTS

Hereinafter, embodiments of the present invention will be described with reference to drawings.

First Embodiment

FIGS. 1 to 9 relate to the first embodiment of the present invention.

Figure 1:
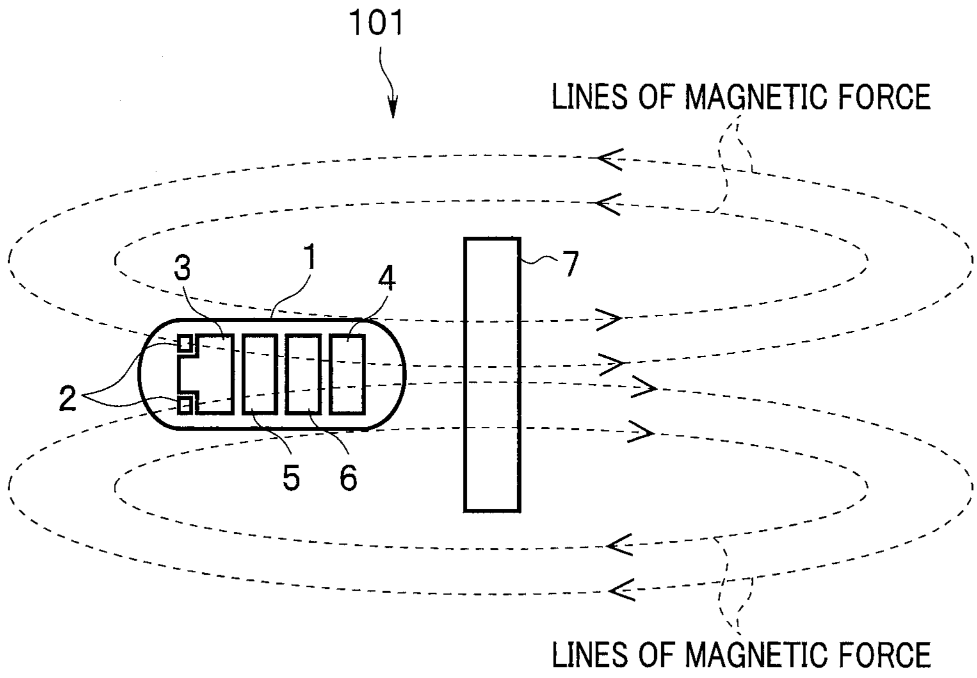
FIG. 1 illustrates a configuration of a main part of a biological information acquiring system according to an embodiment of the present invention.

FIG. 1 illustrates a configuration of a main part of a biological information acquiring system according to the embodiment of the present invention.

A biological information acquiring system 101 includes a biological information acquiring apparatus 1, and a magnetic field generation section 7 which generates an alternate-current magnetic field outside the biological information acquiring apparatus 1, as shown in FIG. 1.

The biological information acquiring apparatus 1 is configured as an apparatus, such as a capsule endoscope, having a dimension, a shape and the like which can be arranged in a body cavity of a subject.

In addition, the biological information acquiring apparatus 1 includes inside thereof: an illumination section 2 which emits illumination light for illuminating an object inside a body cavity of a subject; an image pickup section 3 which picks up an image of an object illuminated by the illumination section 2 and acquires image data; a radio transmission section 4 which modulates image data acquired by the image pickup section 3 into a radio signal and transmits the radio signal outside; a power supplying section 5 which is capable of supplying driving power for driving each of the illumination section 2, the image pickup section 3, and the radio transmission section 4; and a magnetic field detection section 6 which is capable of detecting a magnetic field generated by the magnetic field generation section 7.

That is, a biological information acquiring section according to the present embodiment is configured by including the illumination section 2 and the image pickup section 3.

The magnetic field generation section 7 is configured to be able to generate a burst alternate-current magnetic field for switching the power source state of the biological information acquiring apparatus 1 in response to operations of switches, or the like, not shown. Specifically, the magnetic field generation section 7 is configured to generate a burst alternate-current magnetic field a plurality of times, every time when various types of magnetic field generation switches, to be described later, are turned on once, for example.

Figure 2:
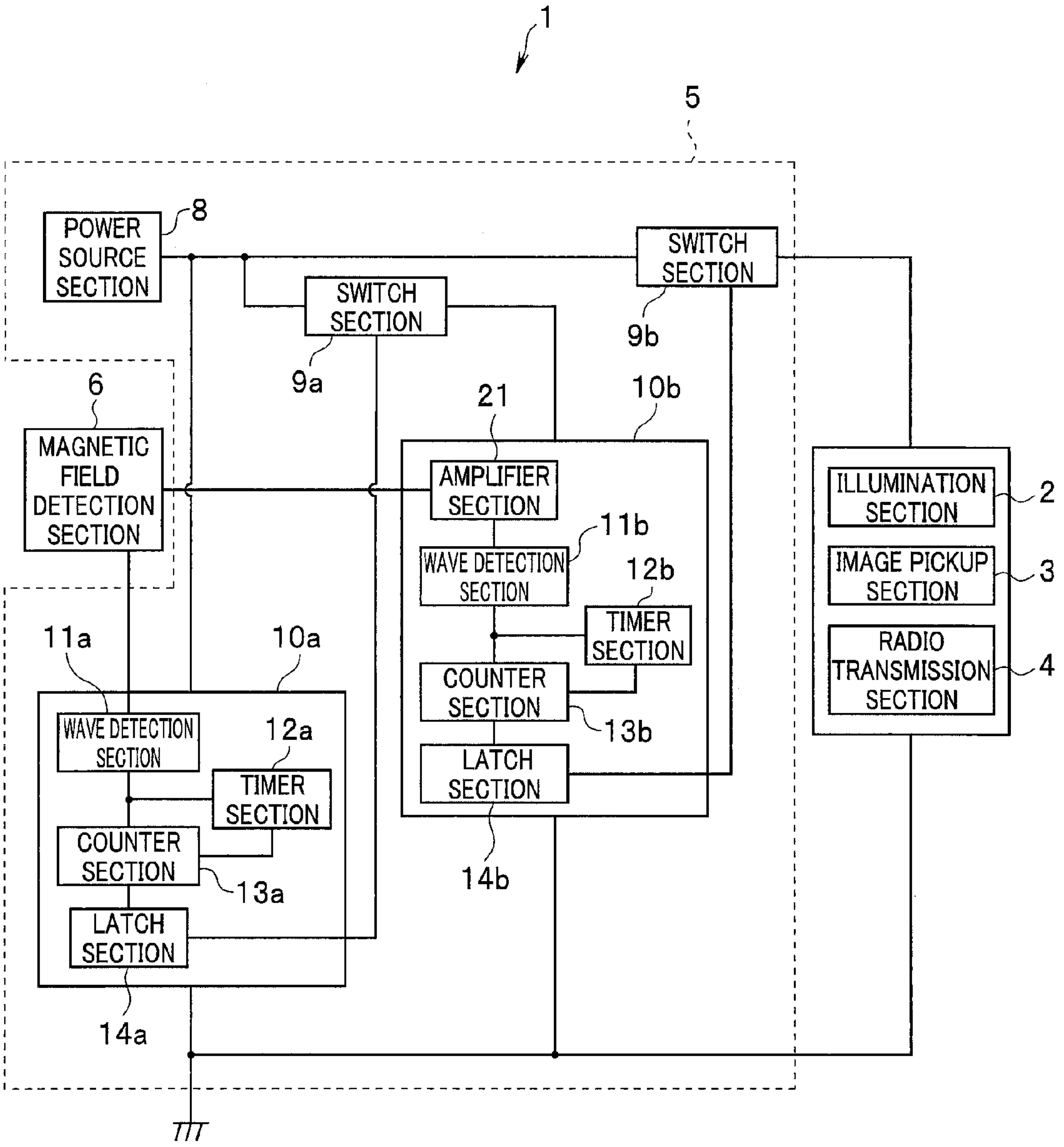
FIG. 2 illustrates one example of an inner configuration of a biological information acquiring apparatus.
Figure 3:
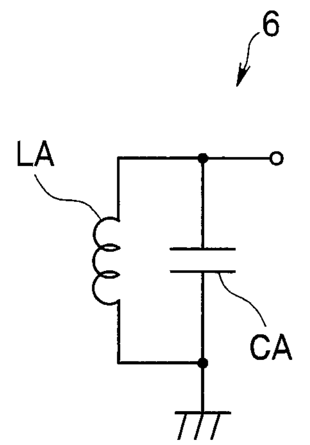
FIG. 3 illustrates one example of a configuration of a magnetic field detection section included in the biological information acquiring apparatus.

FIG. 2 illustrates one example of an inner configuration of a biological information acquiring apparatus. FIG. 3 illustrates one example of the configuration of the magnetic field detection section.

The power supplying section 5, as shown in FIG. 2, is configured by including a power source section 8 constituted of an internal battery or the like which is capable of supplying power for driving each section of the biological information acquiring apparatus 1, switch sections 9*a* and 9*b*, and signal reception sections 10*a*, 10*b*.

The magnetic field detection section 6 is configured as a resonant circuit constituted of a coil LA and a capacitor CA, as shown in FIG. 3, for example. In addition, the magnetic field detection section 6 generates a magnetic field detection signal as an electric signal according to the detection result (waveform at the time of detection) of the alternate-current magnetic field generated from the magnetic field generation section 7 and outputs the generated magnetic field detection signal to the signal reception sections 10*a* and 10*b*.

The power source section 8 is connected so as to supply power to the signal reception section 10*a* on a steady basis, supply power to the signal reception section 10*b* through the switch section 9*a*, and supply power to each of the illumination section 2, the image pickup section 3, and the radio transmission section 4 through the switch section 9*b*.

The switch section 9*a* is connected to the power source section 8, and configured to be turned on or off based on the output state of the switching signal from the signal reception section 10*a* having a function as a first switching control section, thereby capable of switching the supply state of the power from the power source section 8 to the signal reception section 10*b*.

The switch section 9*b* is connected between the switch section 9*a* and the respective sections, i.e., the illumination section 2, the image pickup section 3 and the radio transmission section 4, and configured to be turned on or off based on the output state of the switching signal from the signal reception section 10*b* having a function as a second switching control section, thereby capable of switching the supply state of the power from the power source section 8 to each of the illumination section 2, the image pickup section 3 and the radio transmission section 4.

As shown in FIG. 2, the signal reception section 10*a* is configured by including: a wave detection section 11*a* that detects a magnetic field detection signal having a signal level of a threshold TH1 or above and outputs a pulse signal; a timer section 12*a* that measures a time period from when the wave detection section 11*a* starts outputting the pulse signal until a certain time period TA1 elapses; a counter section 13*a* that acquires a counting value by counting the number of times of input of the pulse signal from the wave detection section 11*a* one by one; and a latch section 14*a* that inverts an output of a switching signal for switching between on and off states of the switch section 9*a* every time the output signal from the counter section 13*a* is inputted.

Figure 4:
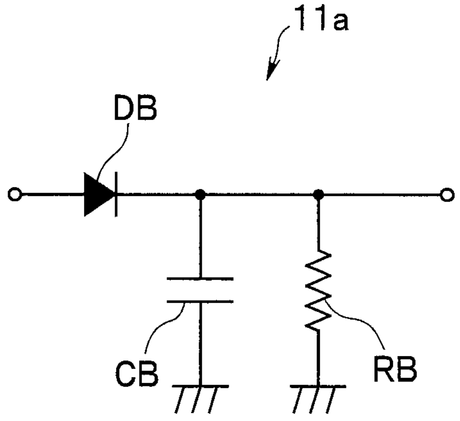
FIG. 4 illustrates one example of a configuration of a wave detection section included in the biological information acquiring apparatus.

FIG. 4 illustrates one example of a configuration of a wave detection section included in the biological information acquiring apparatus.

The wave detection section 11*a* is configured as a peak holding circuit constituted of a diode DB, a capacitor CB, and a resistor RB, as shown in FIG. 4, for example.

That is, the wave detection section 11*a* is configured to appropriately detect the magnetic field detection signal outputted from the magnetic field detection section 6 when the output interval of the magnetic field detection signal outputted from the magnetic field detection section 6 is equal to or greater than a time constant τ1 determined by a product of a capacity of the capacitor CB and a resistance value of the resistor RB. In addition, the wave detection section 11*a* detects the magnetic field detection signal outputted from the magnetic field detection section 6 at each output interval equal to or greater than the time constant τ1, thereby capable of continuously outputting to the counter section 13*a* pulse signals whose number matches the number of times of output of the alternate-current magnetic field outputted in a burst form from the magnetic field generation section 7 (the number of times of output of the magnetic field detection signal outputted from the magnetic field detection section 6).

The timer section 12*a* operates such that the counting value of the counter section 13*a* is reset to zero when the certain time period TA1 has elapsed.

Note that the timer section 12*a* according to the present embodiment is not limited to the one that measures the time period from when the wave detection section 11*a* starts outputting the pulse signal until the certain time period TA1 elapses, but may be configured to measure a time period corresponding to the output interval of the pulse signal outputted from the wave detection section 11*a*, for example, or may be configured to measure these two time periods at the same time. Furthermore, when the timer section 12*a* is configured to measure the time period corresponding to the output interval of the pulse signal outputted from the wave detection section 11*a*, the above-described time constant $\tau 1$ may substantially coincide with the time period measured by the timer section 12*a*.

The counter section 13*a* is configured to output an output signal to the latch section 14*a* when detecting that the counting value, which is acquired by counting the number of times of input of the pulse signal from the wave detection section 11*a* one by one, has reached a signal output counting value PA.

On the other hand, as shown in FIG. 2, the signal reception section 10*b* is configured by including: an amplifier section 21 that amplifies the signal level of the magnetic field detection signal outputted from the magnetic field detection section 6 to a signal level of a threshold TH2 or above; a wave detection section 11*b* that detects the magnetic field detection signal having the signal level of the threshold TH2 or above and outputs a pulse signal; a timer section 12*b* that measures the time period from when the wave detection section 11*b* starts outputting the pulse signal until a certain time period TA2 elapses; a counter section 13*b* that acquires a counting value by counting the number of times of input of the pulse signal from the wave detection section 11*b* one by one; and a latch section 14*b* that inverts an output of a switching signal for switching between the on and off states of the switch section 9*b* every time the output signal from the counter section 13*b* is inputted.

Figure 5:
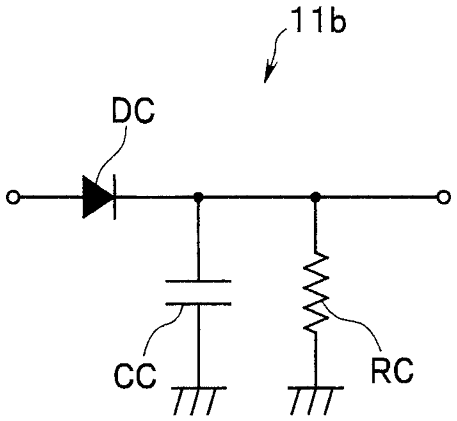
FIG. 5 illustrates one example of a configuration of another wave detection section included in the biological information acquiring apparatus.

FIG. 5 illustrates one example of a configuration of another wave detection section included in the biological information acquiring apparatus.

The wave detection section 11*b* is configured as a peak holding circuit constituted of a diode DC, a capacitor CC, and a resistor RC, as shown in FIG. 5, for example.

That is, the wave detection section 11*b* is configured to appropriately detect the magnetic field detection signal outputted from the magnetic field detection section 6 when the output interval of the magnetic field detection signal outputted from the magnetic field detection section 6 is equal to or greater than a time constant $\tau 2$ determined by a product of a capacity of the capacitor CC and a resistance value of the resistor RC. In addition, the wave detection section 11*b* detects the magnetic field detection signal outputted from the magnetic field detection section 6 at each output interval equal to or greater than the time constant $\tau 2$, thereby capable of continuously outputting to the counter section 13*b* pulse signals whose number matches the number of times of output of the alternate-current magnetic field outputted in a burst form from the magnetic field generation section 7 (the number of times of output of the magnetic field detection signal outputted from the magnetic field detection section 6).

The timer section 12*b* operates such that the counting value of the counter section 13*b* is reset to zero when the certain time period TA2 has elapsed.

Note that the timer section 12*b* according to the present embodiment is not limited to the one that measures the time period from when the wave detection section 11*b* starts outputting the pulse signal until the certain time period TA2 elapses, but may be configured to measure a time period corresponding to the output interval of the pulse signal outputted from the wave detection section 11*b*, for example, or may be configured to measure these two time periods at the same time. Furthermore, when the timer section 12*b* is configured to measure the time period corresponding to the output interval of the pulse signal outputted from the wave detection section 11*b*, the above-described time constant $\tau 2$ may coincide with the time period measured by the timer section 12*b*.

In addition, according to the present embodiment, the above-described certain time periods TA1 and TA2 may be set to the same time period, or set such that TA1 is longer than TA2.

The counter section 13*b* is configured to output an output signal to the latch section 14*b* when detecting that the counting value, which is acquired by counting the number of times of input of the pulse signal from the wave detection section 11*b* one by one, has reached a signal output counting value PB.

Note that the above-described signal output counting values PA and PB may be set to arbitrary values, respectively, as long as these values have a magnitude relationship of PA>PB.

In addition, in the present embodiment, it is supposed that the capacities of the capacitors CB and CC and resistance values of the resistors RB and RC are respectively set such that the time constant $\tau 1$ of the wave detection section 11*a* and the time constant $\tau 2$ of the wave detection section 11*b* have the same value.

Figure 6:
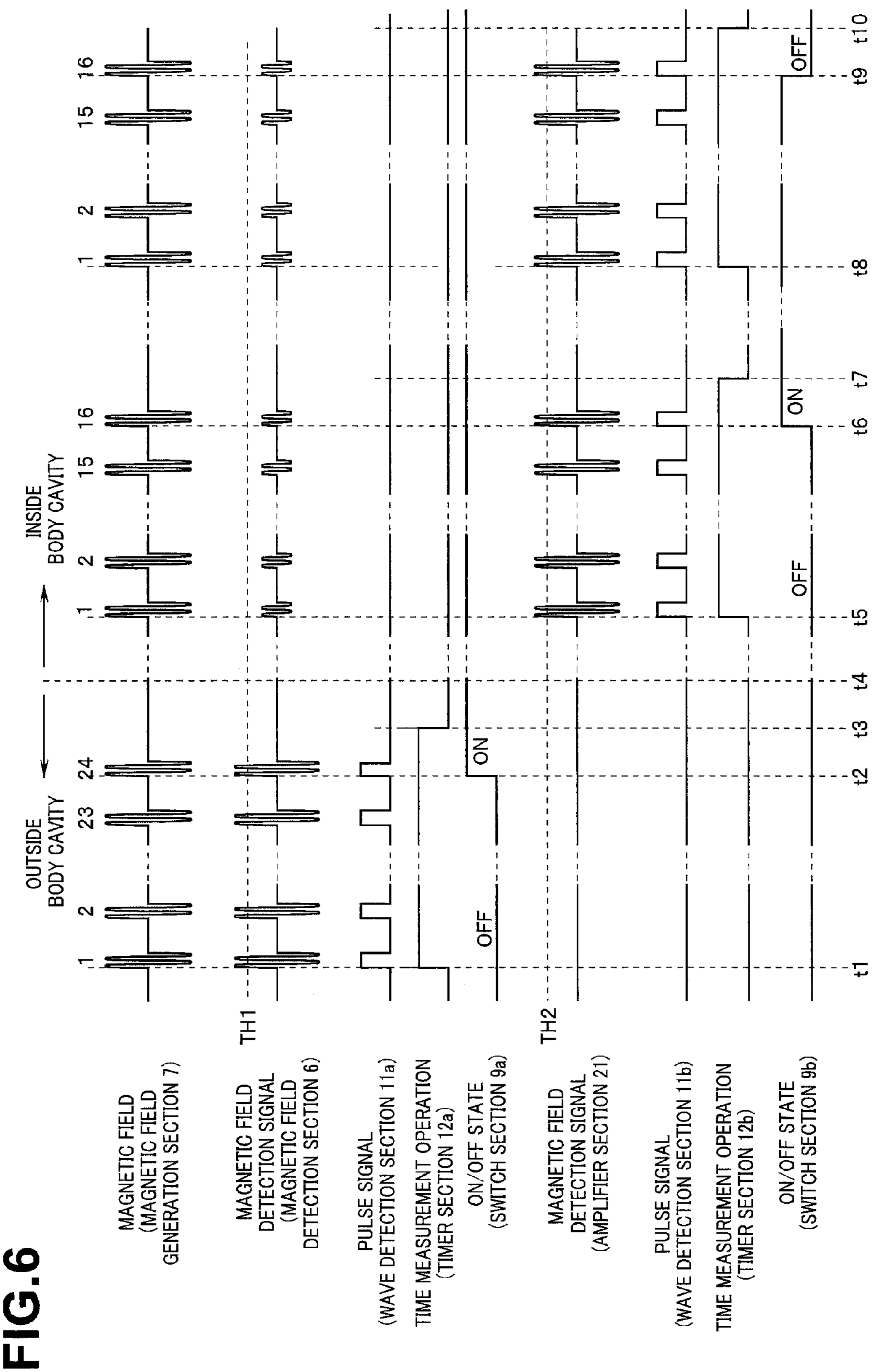
FIG. 6 illustrates a timing chart for describing one example of an operation of the biological information acquiring apparatus according to a first embodiment.

Here, detailed description will be made on a case where the biological information acquiring apparatus 1 is arranged in a body cavity of a subject with reference to the timing chart in FIG. 6 as needed. FIG. 6 illustrates a timing chart for describing one example of an operation of the biological information acquiring apparatus according to the first embodiment.

Note that in the explanation related to the timing chart in FIG. 6, description will be made, for simplification, supposing that each of the latch sections 14*a* and 14*b* is configured by a D flip-flop and operates in synchronization with rising of signals. Furthermore, in the explanation related to the timing chart in FIG. 6, description will be made, for simplification, by taking a case where the value of the above-described signal output counting value PA is 24, and the above-described signal output counting value PB is 16, as an example.

First, in an initial state corresponding to the period before a time t1, no alternate-current magnetic field is generated from the magnetic field generation section 7. As a result, both of the switch sections 9*a* and 9*b* are in an off state. In the initial state like this, power is supplied from the power source section 8 to the signal reception section 10*a*, whereas power is not supplied from the power source section 8 to each of the illumination section 2, the image pickup section 3, the radio transmission section 4, and the signal reception section 10*b*. In addition, in the above-described initial state, the operation of each of the illumination section 2, the image pickup section 3, the radio transmission section 4, and the signal reception section 10*b* is completely stopped, and the signal reception section 10*a* hardly operates, since no alternate-current magnetic field is generated from the magnetic field generation section 7. Therefore, in the above-described initial state, input-standby state of the magnetic field detection signal from the magnetic field detection section 6 is maintained with the consumption of the power supplied from the power source section 8 limited to the minimum.

Then, when a first magnetic field generation switch (not shown) provided on the magnetic field generation section 7 is turned on by an operator or the like at the time t1, for example, a first generation of the burst alternate-current magnetic field, out of the total 24 times of generations of the burst alternate-current magnetic field each of which is performed once in a predetermined cycle, is performed by the magnetic field generation section 7.

In addition, when the first generation, out of the total 24 times of generations, of the burst alternate-current magnetic field is performed by the magnetic field generation section 7 at the time t1, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and time measurement operation for measuring the certain time period TA1 is started in the timer section 12*a*. Furthermore, in accordance with such operations performed at the time t1, the counting value of the counter section 13*a* is updated to 1.

After that, when the 24th generation, out of the total 24 times of generations, of the burst alternate-current magnetic field is performed by the magnetic field generation section 7 at the time t2, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t2, the counting value of the counter section 13*a* is updated to 24, the output signal outputted from the counter section 13*a* is inputted to the latch section 14*a*, the switching signal outputted from the latch section 14*a* is inverted, and the switch section 9*a* is switched from OFF to ON.

Therefore, according to the operations of the respective sections, when the time reaches the time t2, the switch section 9*a* is turned on, thereby starting the supply of the power from the power source section 8 to the signal reception section 10*b*.

Note that, since power is not supplied to the signal reception section 10*b* before the time t2, even if the magnetic field detection signal from the magnetic field detection section 6 is inputted to (the amplifier section 21 of) the signal reception section 10*b*, the switching signal is not outputted from the latch section 14*b* and the switch section 9*b* is maintained in the off state.

On the other hand, the timer section 12*a* operates such that the counting value of the counter section 13*a* is reset to zero, when completing the time measurement operation for measuring the certain time period TA1 at a time t3 after the time t2. In other words, in the case where the counting value of the counter section 13*a* does not reach 24 before the certain time period TA1 corresponding to the period from the time t1 to the time t3 elapses, the counting value of the counter section 13*a* is reset to zero, and thereby the switching signal outputted from the latch section 14*a* is maintained without being inverted. As a result, since the switch section 9*a* is not switched from OFF to ON, supply of the power from the power source section 8 to the signal reception section 10*b* is not started.

Subsequently, at a time t4 after the time t3, the biological information acquiring apparatus 1 is arranged in the body cavity of the subject by the subject swallowing the biological information acquiring apparatus 1.

After that, when the second magnetic field generation switch (not shown) provided on the magnetic field generation section 7 is turned on by the operator or the like, for example, at a time t5, the first generation of the burst alternate-current magnetic field, out of total 16 times of generations of the burst alternate-current magnetic field each of which is performed once in a predetermined cycle, is performed by the magnetic field generation section 7.

In addition, when the first generation, out of total 16 times of generations, of the burst alternate-current magnetic field is performed by the magnetic field generation section 7 at the time t5, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t5, the counting value of the counter section 13*b* is updated to 1.

After that, when the 16th generation, out of the total 16 times of generations, of the burst alternate-current magnetic field is performed by the magnetic field generation section 7 at a time t6, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t6, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from OFF to ON.

Therefore, according to the above-described operations of the respective sections, when the time reaches the time t6, the switch section 9*b* is turned on, thereby starting the supply of the power from the power source section 8 to the illumination section 2, the image pickup section 3 and the radio transmission section 4, that is, resulting in a transition to a state where the image data in the body cavity of the subject can be acquired.

Note that, after the time t5, since the biological information acquiring apparatus 1 is arranged in the body cavity of the subject, the signal level of the magnetic field detection signal outputted from the magnetic field detection section 6 becomes smaller than the threshold TH1 which can be detected in the wave detection section 11*a*. Therefore, after the time t5, even if the magnetic field detection signal from the magnetic field detection section 6 is inputted to (the wave detection section 11*a*) of the signal reception section 10*a* while the biological information acquiring apparatus 1 is arranged in the body cavity of the subject, the switching signal outputted from the latch section 14*a* is not inverted, and the switch section 9*a* is maintained in the on state.

On the other hand, the timer section 12*b* operates such that the counting value of the counter section 13*b* is reset to zero, when completing the time measurement operation for measuring the certain time period TA2 at a time t7 after the time t6. In other words, in the case where the counting value of the counter section 13*b* does not reach 16 before the certain time period TA2 corresponding to the period from the time t5 to the time t7 elapses, the counting value of the counter section 13*b* is reset to zero, and thereby the switching signal outputted from the latch section 14*b* is maintained without being inverted. As a result, since the switch section 9*b* is not switched from OFF to ON, supply of the power from the power source section 8 to each of the illumination section 2, the image pickup section 3 and the radio transmission section 4 is not started.

After that, when the second magnetic field generation switch (not shown) provided on the magnetic field generation section 7 is turned on again by the operator or the like at a time t8, for example, the first generation of the burst alternate-current magnetic field, out of total 16 times of generations of the burst alternate-current magnetic field each of which is performed once in a predetermined cycle, is performed by the magnetic field generation section 7.

In addition, when the first generation, out of the total 16 times of generations, of the burst alternate-current magnetic field is performed by the magnetic field generation section 7 at the time t8, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t8, the counting value of the counter section 13*b* is updated to 1.

After that, when the 16th generation, out of the total 16 times of generations, of the burst alternate-current magnetic field is performed by the magnetic field generation section 7 at a time t9, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t9, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from ON to OFF.

Therefore, according to the above-described operations of the respective sections, when the time reaches the time t9, the switch section 9*b* is switched from ON to OFF, thereby stopping the supply of the power from the power source section 8 to each of the illumination section 2, the image pickup section 3, and the radio transmission section 4, that is, resulting in a transition from the state where the image data inside the body cavity of the subject can be acquired to the state where the image data inside the body cavity of the subject cannot be acquired.

In addition, according to the above-described operations from the time t8 to the time t9, in a case where it is found out that the biological information acquiring apparatus 1 has not reached a desired region to be observed by causing the image data acquired after the time t7 to be displayed on a monitor or the like, not shown, for example, and confirming the displayed image data, it is possible to once stop the supply of power to each of the illumination section 2, the image pickup section 3 and the radio transmission section 4.

On the other hand, the timer section 12*b* operates such that the counting value of the counter section 13*b* is reset to zero, when completing the time measurement operation for measuring the certain time period TA2 at a time t10 after the time t9. In other words, in the case where the counting value of the counter section 13*b* does not reach 16 before the certain time period TA2 corresponding to the period from the time t8 to the time t10 elapses, the counting value of the counter section 13*b* is reset to zero, and thereby the switching signal outputted from the latch section 14*b* is maintained without being inverted. As a result, since the switch section 9*b* is not switched from ON to OFF, the supply of the power from the power source section 8 to each of the illumination section 2, the image pickup section 3 and the radio transmission section 4 is continued.

That is, according to the above-described operations from the time t5 to the time t10, in accordance with ON/OFF switching of the second magnetic field generation switch (not shown) by the operator or the like in the case where the switch section 9*a* is in the on state, ON/OFF state of the switch section 9*b* is switched. Therefore, according to the operations from the time t5 to the time t10, the operations related to the supply of the power from the power source section 8 to each of the illumination section 2, the image pickup section 3 and the radio transmission section 4 can be regarded as a toggle operation in accordance with the ON/OFF switching of the second magnetic field generation switch (not shown).

Figure 7:
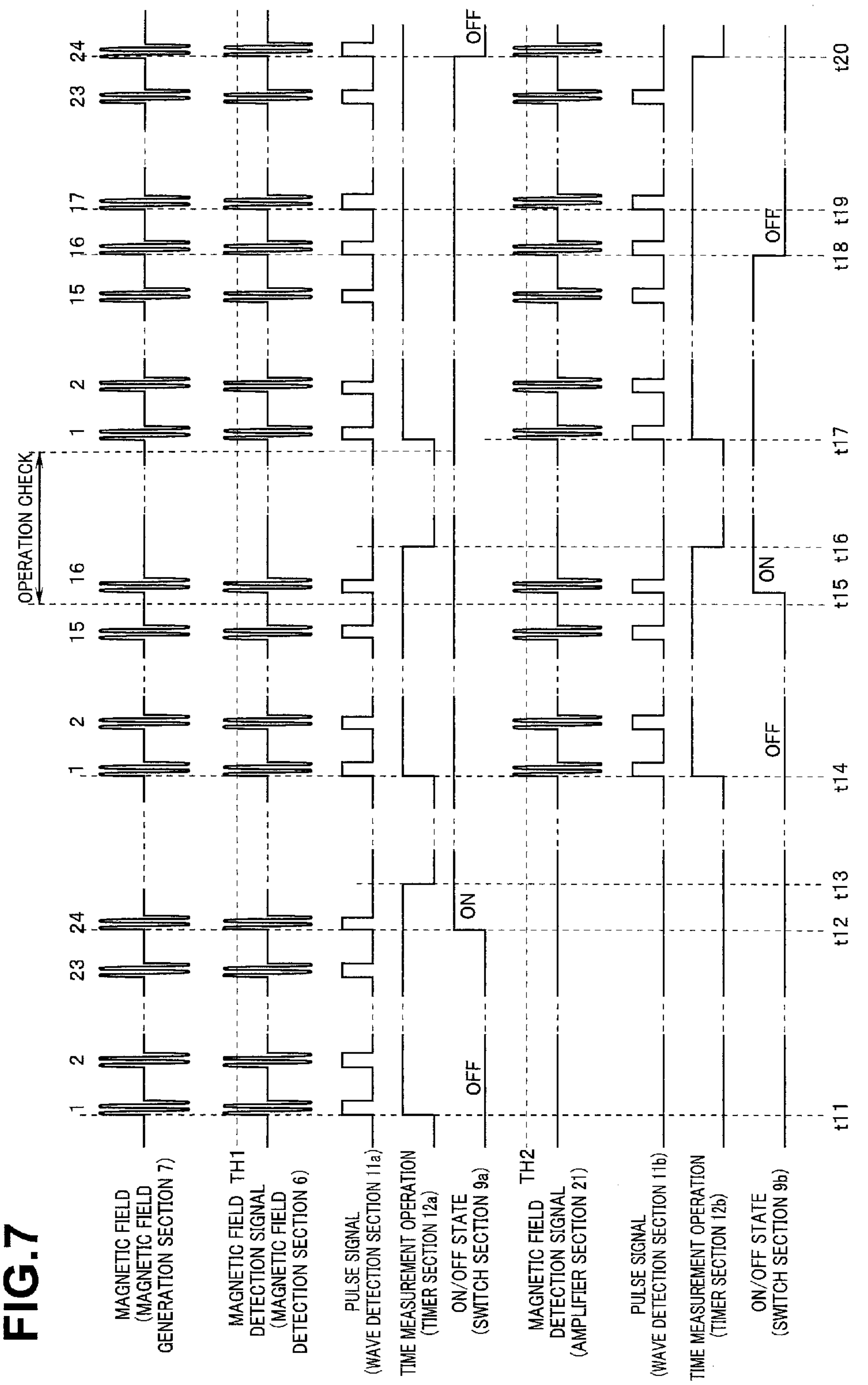
FIG. 7 illustrates a timing chart for describing an example, which is different from the example shown in FIG. 6, of the operation of the biological information acquiring apparatus according to the first embodiment.

Next, detailed description will be made on the case where operation check is performed before the biological information acquiring apparatus 1 is arranged in the body cavity of the subject, with reference to the timing chart in FIG. 7 as appropriate. FIG. 7 illustrates a timing chart for describing an example, which is different from the example shown in FIG. 6, of the operation of the biological information acquiring apparatus according to the first embodiment.

Note that, in the description related to the timing chart in FIG. 7, description will be made, for simplification, supposing that each of the latch sections 14*a* and 14*b* is configured by a D flip-flop and operates in synchronization with rising of signals. In addition, in the description related to the timing chart in FIG. 7, description will be made, for simplification, by taking the case where the value of the above-described signal output counting value PA is 24, and the above-described signal output counting value PB is 16, as an example. Furthermore, in the description related to the timing chart in FIG. 7, description will be made by taking the above-described case where TA1 is equal to TA2 as an example, for simplification.

First, in an initial state corresponding to the period before the time t11, since no alternate-current magnetic field is generated from the magnetic field generation section 7, both of the switch sections 9*a* and 9*b* are in the off state. In the initial state like this, power is supplied from the power source section 8 to the signal reception section 10*a*, whereas the power is not supplied from the power source section 8 to each of the illumination section 2, the image pickup section 3, the radio transmission section 4 and the signal reception section 10*b*.

Then, when the first magnetic field generation switch (not shown) provided on the magnetic field generation section 7 is turned on by the operator or the like, for example, at the time t11, the first generation of the burst alternate-current magnetic field, out of the total 24 times of generations of the burst alternate-current magnetic field each of which is performed once in a predetermined cycle, is performed by the magnetic field generation section 7.

In addition, when the first generation, out of the total 24 times of generations, of the burst alternate-current magnetic field is performed by the magnetic field generation section 7 at the time t11, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. Furthermore, in accordance with such operations performed at the time t11, the counting value of the counter section 13*a* is updated to 1.

After that, when the 24th generation, out of the total 24 times of generations, of the burst alternate-current magnetic field is performed by the magnetic field generation section 7 at a time t12, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t12, the counting value of the counter section 13*a* is updated to 24, the output signal outputted from the counter section 13*a* is inputted to the latch section 14*a*, the switching signal outputted from the latch section 14*a* is inverted, and the switch section 9*a* is switched from OFF to ON.

Therefore, according to the above-described operations of the respective sections, when the time reaches the time t12, the switch section 9*a* is turned on, and thereby supply of the power from the power source section 8 to the signal reception section 10*b* is started.

Note that, before the time 12, since power is not supplied to the signal reception section 10*b*, even if the magnetic field detection signal from the magnetic field detection section 6 is inputted to (the amplifier section 21 of) the signal reception section 10*b*, the switching signal is not outputted from the latch section 14*b*, and the switch section 9*b* is maintained in the off state.

On the other hand, the timer section 12*a* operates such that the counting value of the counter section 13*a* is reset to zero, when completing the time measurement operation for measuring the certain time period TA1 at a time t13 after the time t12. In other words, in the case where the counting value of the counter section 13*a* does not reach 24 before the certain time period TA1 corresponding to the period from the time t11 to the time t13 elapses, the counting value of the counter section 13*a* is reset to zero, and thereby the switching signal outputted from the latch section 14*a* is maintained without being inverted. As a result, since the switch section 9*a* is not switched from OFF to ON, supply of the power from the power source section 8 to the signal reception section 10*b* is not started.

Subsequently, when the second magnetic field generation switch (not shown) provided on the magnetic field generation section 7 is turned on by the operator or the like, for example, at a time t14 after the time t13, the first generation of the burst alternate-current magnetic field, out of the total 16 times of generations of the burst alternate-current magnetic field each of which is performed once in a predetermined cycle, is performed by the magnetic field generation section 7.

Furthermore, when the first generation, out of the total 16 times of generations, of the burst alternate-current magnetic field is performed by the magnetic field generation section 7, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t14, the counting value of the counter section 13*b* is updated to 1.

After that, when the 16th generation, out of the total 16 times of generations, of the burst alternate-current magnetic field is performed by the magnetic field generation section 7 at the time t15, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t15, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from OFF to ON.

Therefore, according to the above-described operations of the respective sections, when the time reaches the time t15, the switch section 9*b* is turned on, thereby starting the supply of the power from the power source section 8 to each of the illumination section 2, the image pickup section 3 and the radio transmission section 4, that is, resulting in a transition to a state where the operation check of the biological information acquiring apparatus 1 is possible.

On the other hand, the timer section 12*a* operates such that the counting value of the counter section 13*a* is reset to zero, when completing the time measurement operation for measuring the certain time period TA1 at a time t16 after the time t15. In addition, the timer section 12*b* operates such that the counting value of the counter section 13*b* is reset to zero, when completing the time measurement operation for measuring the certain time period TA2 at the time t16 after the time t15.

After the time t14, since the biological information acquiring apparatus 1 has not been arranged in the body cavity of the subject yet, the signal level of the magnetic field detection signal outputted from the magnetic field detection section 6 becomes equal to or higher than the threshold TH1 which can be detected in the wave detection section 11*a*. However, when the certain time period TA1 corresponding to the period from the time t14 to the time t16 elapses, the counting value of the counter section 13*a*, which has not reached 16, is reset to zero. Therefore, the switching signal outputted from the latch section 14*a* is not inverted even after the time t16, that is, the switch section 9*a* is maintained in the on state even after the time t16.

Subsequently, when the first magnetic field generation switch (not shown) provided on the magnetic field generation section 7 is turned on again by the operator or the like, for example, at the time t17 after the completion of the operation check of the biological information acquiring apparatus 1, the first generation of the burst alternate-current magnetic field, out of the total 24 times of generations of the burst alternate-current magnetic field each of which is performed once in a predetermined cycle, is performed by the magnetic field generation section 7.

Then, when the first generation, out of the total 24 times of generations, of the burst alternate-current magnetic field is performed by the magnetic field generation section 7 at the time t17, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. In addition, in accordance with the first generation, out of the total 24 times of generations, of the burst alternate-current magnetic field performed by the magnetic field generation section 7 at the time t17, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t17, the counting values of the counter section 13*a* and the counter section 13*b* are respectively updated to 1.

After that, when the 16th generation, out of the total 24 times of generations, of the burst alternate-current magnetic field is performed by the magnetic field generation section 7 at a time t18, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t18, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from ON to OFF.

In addition, when the 24th generation, out of the total 24 times of generations, of the burst alternate-current magnetic field is performed by the magnetic field generation section 7 at a time t20 after the time t18, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t20, the counting value of the counter section 13*a* is updated to 24, the output signal outputted from the counter section 13*a* is inputted to the latch section 14*a*, the switching signal outputted from the latch section 14*a* is inverted, and the switch section 9*a* is switched from ON to OFF.

Note that, when the 17th generation, out of total 24 times of generations, of the burst alternate-current magnetic field is performed by the magnetic field generation section 7 after the time t19 substantially immediately after the time t18, the counting value of the counter section 13*b* increases again one by one. However, when the switch section 9*a* is turned off substantially immediately after the time 20, the supply of the power to the signal reception section 10*b* is stopped and the switching signal is not outputted from the latch section 14*b*. As a result, the switch section 9*b* is maintained in the off state even after the time t20.

Therefore, the operator or the like performs operation check of the biological information acquiring apparatus 1 before arranging the biological information acquiring apparatus in the body cavity of the subject, and thereafter operates the first magnetic field generation switch provided on the magnetic field generation section 7, thereby capable of bringing the power source state of the biological information acquiring apparatus 1 from a high power consumption state in which each of the illumination section 2, the image pickup section 3 and the radio transmission section 4 is activated to a low power consumption state corresponding to the input standby state of the magnetic field detection signal from the magnetic field detection section 6 all at once.

As described above, the present embodiment provides a configuration which allows a control for changing the power source state of the biological information acquiring apparatus to be changed based on the number of times of output of the magnetic field detection signal outputted according to the detection result of the alternate-current magnetic field generated in a burst form. Therefore, according to the present embodiment, it is possible to switch ON and OFF of the power source of the biological information acquiring apparatus more surely than in conventional apparatuses, without increasing the size of the antenna incorporated into the biological information acquiring apparatus, for example.

Note that, according to the present embodiment, in addition to the above-described first and second magnetic field generation switches, a third magnetic field generation switch (not shown) which allows total 40 times of generations of the burst alternate-current magnetic field each of which is performed once in a predetermined cycle may be provided on the magnetic field generation section 7, for example.

Figure 8:
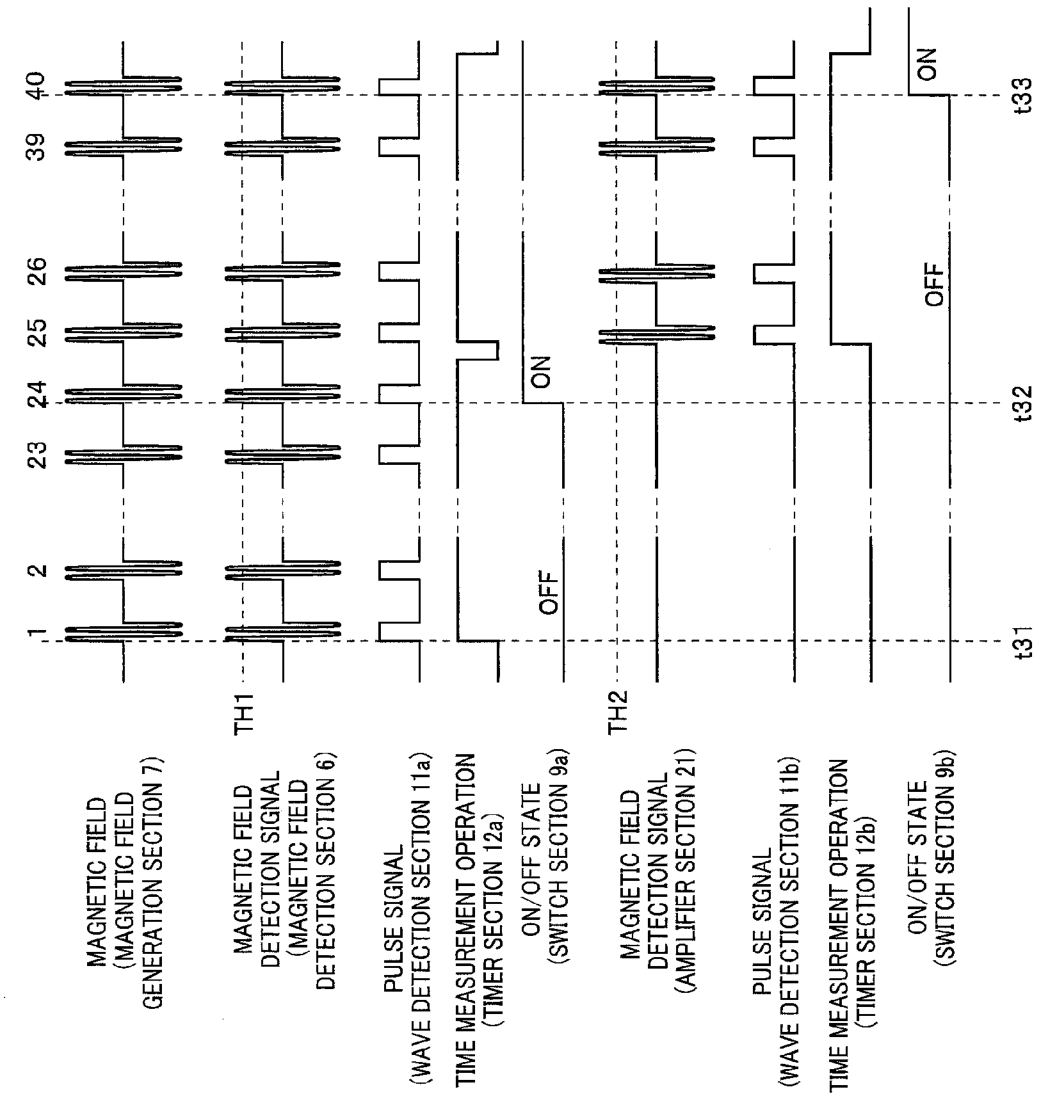
FIG. 8 illustrates a timing chart for describing an example, which is different from the examples shown in FIG. 6 and FIG. 7, of the operation of the biological information acquiring apparatus according to the first embodiment.
Figure 9:
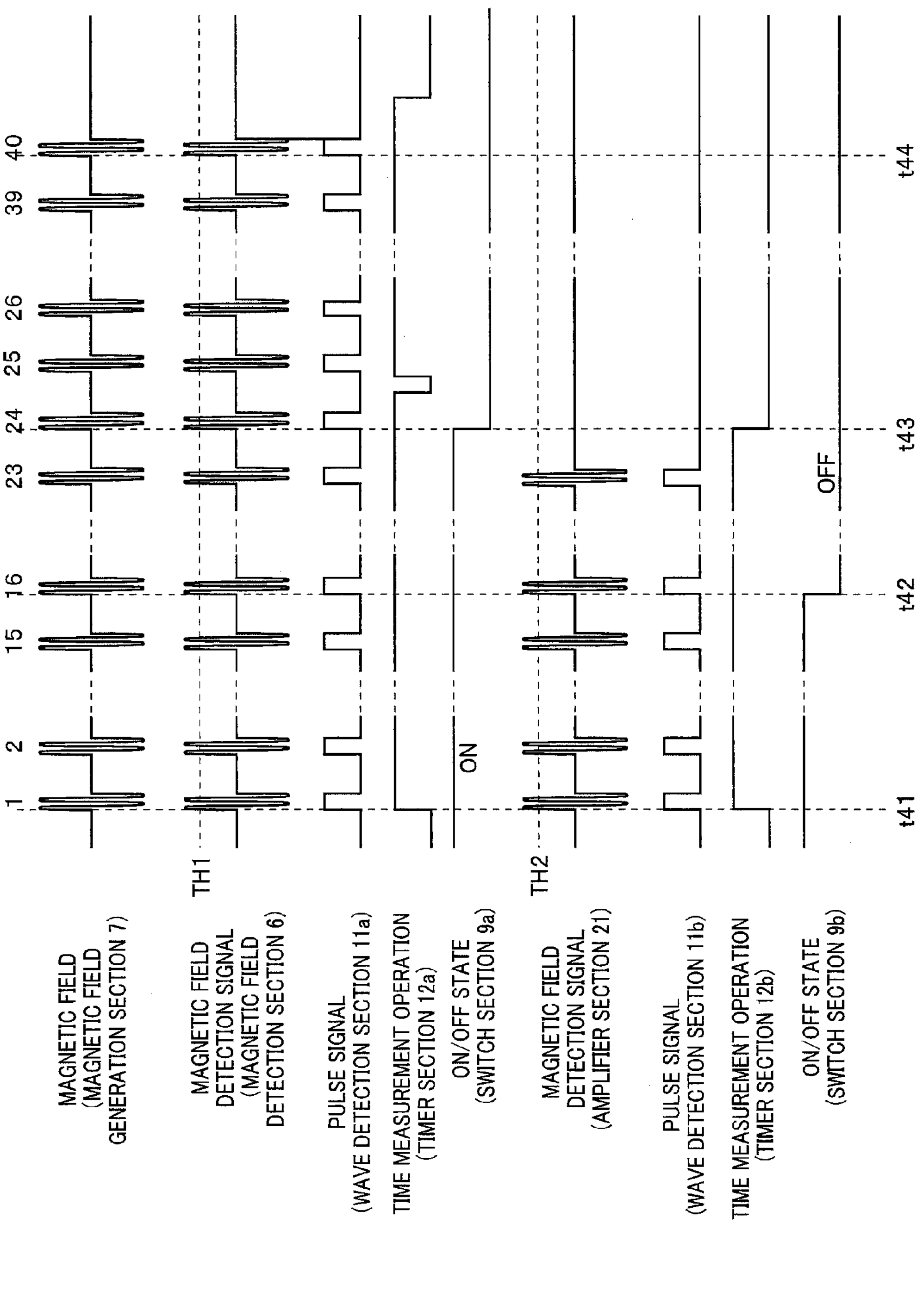
FIG. 9 illustrates a timing chart for describing an example, which is different from the examples shown in FIG. 6, FIG. 7 and FIG. 8, of the operation of the biological information acquiring apparatus according to the first embodiment.

Now, detailed description will be made on the case where the power source state of the biological information acquiring apparatus 1 is changed in response to the operation of the third magnetic field generation switch before arranging the biological information acquiring apparatus 1 in the body cavity of the subject, with reference to the timing charts in FIGS. 8 and 9. FIG. 8 illustrates a timing chart for describing an example, which is different from the examples shown in FIG. 6 and FIG. 7, of the operation of the biological information acquiring apparatus according to the first embodiment. FIG. 9 illustrates a timing chart for describing an example, which is different from the examples shown in FIG. 6, FIG. 7 and FIG. 8, of the operation of the biological information acquiring apparatus according to the first embodiment.

Note that, in the description related to the timing charts in FIGS. 8 and 9, description will be made, for simplification, supposing that each of the latch sections 14*a* and 14*b* is configured by a D flip-flop and operates in synchronization with rising of signals. In addition, in the description related to the timing charts in FIGS. 8 and 9, description will be made, for simplification, by taking the case where the value of the above-described signal output counting value PA is 24, and the above-described signal output counting value PB is 16, as an example. Furthermore, in the description related to the timing charts in FIGS. 8 and 9, description will be made, for simplification, by taking the above-described case where TA1 is equal to TA2 as an example.

First, in an initial state corresponding to the period before a time t31, since no alternate-current magnetic field is generated from the magnetic field generation section 7, both of the switch sections 9*a* and 9*b* are in the off state. In addition, in the initial state like this, power is supplied from the power source section 8 to the signal reception section 10*a*, whereas the power from the power source section 8 is not supplied to each of the illumination section 2, the image pickup section 3, the radio transmission section 4 and the signal reception section 10*b*.

Then, when the third magnetic field generation switch (not shown) provided on the magnetic field generation section 7 is turned on by the operator or the like at the time t31, the first generation of the burst alternate-current magnetic field, out of total 40 times of generations each of which is performed once in a predetermined cycle, is performed by the magnetic field generation section 7.

In addition, when the first generation, out of the total 40 times of generations, of the burst alternate-current magnetic field is performed by the magnetic field generation section 7 at the time t31, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. Furthermore, in accordance with such operations performed at the time t31, the counting value of the counter section 13*a* is updated to 1.

After that, when the 24th generation, out of the total 40 times of generations, of the burst alternate-current magnetic field is performed by the magnetic field generation section 7 at a time t32, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t32, the counting value of the counter section 13*a* is updated to 24, the output signal outputted from the counter section 13*a* is inputted to the latch section 14*a*, the switching signal outputted from the latch section 14*a* is inverted, and the switch section 9*a* is switched from OFF to ON.

The timer section 12*a* operates such that the counting value of the counter section 13*a* is reset to zero, when completing the time measurement operation for measuring the certain time period TA1 substantially immediately after the time t32.

Then, when the 40th generation, out of the total 40 times of generations, of the burst alternate-current magnetic field is performed by the magnetic field generation section 7 at a time t33, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t33, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from OFF to ON.

Note that, after the time t33, when the biological information acquiring apparatus 1 is arranged in the body cavity of the subject and the second magnetic field generation switch (not shown) provided on the magnetic field generation section 7 is turned on by the operator or the like, for example, similar operations as those in the period from the time t8 to the time t9 in FIG. 6 are performed, and thereby the switch section 9*b* is switched from ON to OFF and the supply of the power source to each of the illumination section 2, the image pickup section 3 and the radio transmission section 4 is stopped.

On the other hand, at a time t41 after the time t33, when the third magnetic field generation switch (not shown) provided on the magnetic field generation section 7 is turned on by the operator or the like, the first generation of the burst alternate-current magnetic field, out of the total 40 times of generations of the burst alternate-current magnetic field each of which is performed once in a predetermined cycle, is performed by the magnetic field generation section 7.

Then, when the first generation, out of the total 40 times of generations, of the burst alternate-current magnetic field is performed by the magnetic field generation section 7 at the time t41, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. Furthermore, when the first generation, out of the total 40 times of generations, of the burst alternate-current magnetic field is performed by the magnetic field generation section 7 at the time t41, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t41, the counting values of the counter section 13*a* and the counter section 13*b* are respectively updated to 1.

After that, when the 16th generation, out of the total 40 times of generations, of the burst alternate-current magnetic field is performed by the magnetic field generation section 7 at a time t42, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t42, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from ON to OFF.

In addition, when the 24th generation, out of the total 40 times of generations, of the burst alternate-current magnetic field is performed by the magnetic field generation section 7 at a time t43, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t43, the counting value of the counter section 13*a* is updated to 24, the output signal outputted from the counter section 13*a* is inputted to the latch section 14*a*, the switching signal outputted from the latch section 14*a* is inverted, and the switch section 9*a* is switched from ON to OFF.

The timer section 12*a* operates such that the counting value of the counter section 13*a* is reset to zero, when completing the time measurement operation for measuring the certain time period TA1 substantially immediately after the time t43.

Note that, even after the time t42, the time measurement operation by the timer section 12*b* and the acquisition of the counting value of the counter section 13*b* are continuously performed. However, when the switch section 9*a* is turned off substantially immediately after the time t43, supply of the power to the signal reception section 10*b* is stopped and the switching signal is not outputted from the latch section 14*b*. As a result, the switch section 9*b* is maintained in the off state even after the time t43.

In addition, when the 25th generation, out of the total 40 times of generations, of the burst alternate-current magnetic field is performed by the magnetic field generation section 7 after the time t43, the counting value of the counter section 13*a* increases again one by one. However, when the 40th generation, out of the total 40 times of generations, of the burst alternate-current magnetic field is performed by the magnetic field generation section 7 at a time t44 after the time t43, the counting value of the counter section 13*a* does not reach 24 in a period during which the certain time period TA1 is measured. As a result, the switching signal outputted from the latch section 14*a* is not inverted even after the time t44, that is, the switch section 9*a* is maintained in the off state even after the time t44.

That is, according to the above-described configuration in which the power source state of the biological information acquiring apparatus 1 can be switched in response to the operation of the third magnetic field generation switch provided on the magnetic field generation section 7, it is possible to easily visually confirm whether the biological information acquiring apparatus 1 is in the on state or off state before arranging the biological information acquiring apparatus 1 in the body cavity of the subject.

Note that the present embodiment shows an example in which the first magnetic field generation switch, the second magnetic field generation switch, and the third magnetic field generation switch (all not shown) are provided on the magnetic field generation section 7 and the burst alternate-current magnetic field is generated for a number of times according to the operations of the respective switches. However, the present embodiment is not limited to such a configuration. Specifically, coils, each of which generates the burst alternate-current magnetic field 16 times, 24 times and 40 times, may be integrally configured, or a part of or all of the coils may be configured as separated bodies, for example. In addition, apparatuses, each of which generates the burst alternate-current magnetic field 16 times, 24 times, and 40 times, may be integrally configured (like the magnetic field generation section 7), or a part of or all of the apparatuses may be configured as separated bodies, for example.

Second Embodiment

Figure 10:
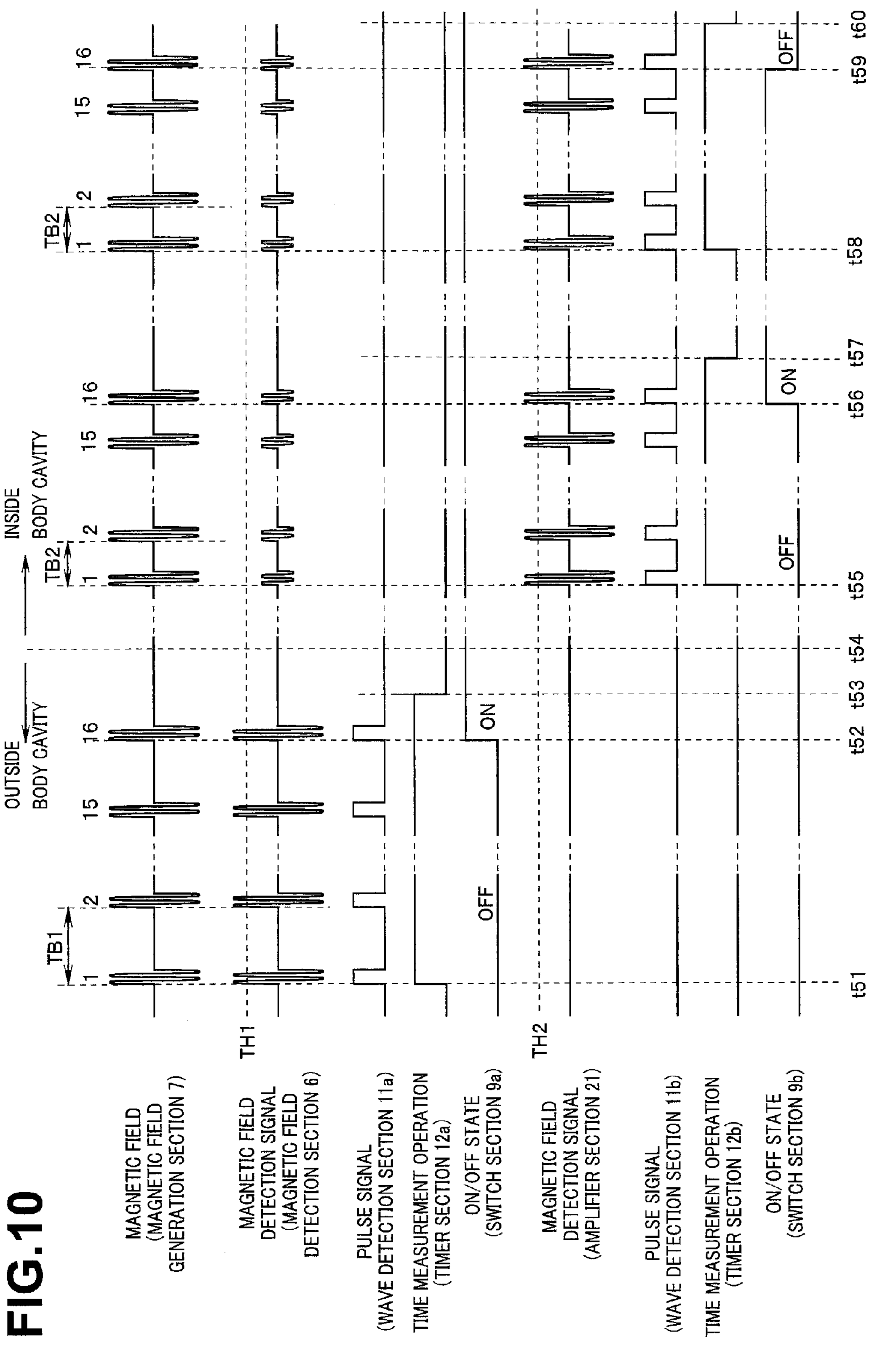
FIG. 10 illustrates a timing chart for describing an example of an operation of a biological information acquiring apparatus according to a second embodiment.
Figure 11:
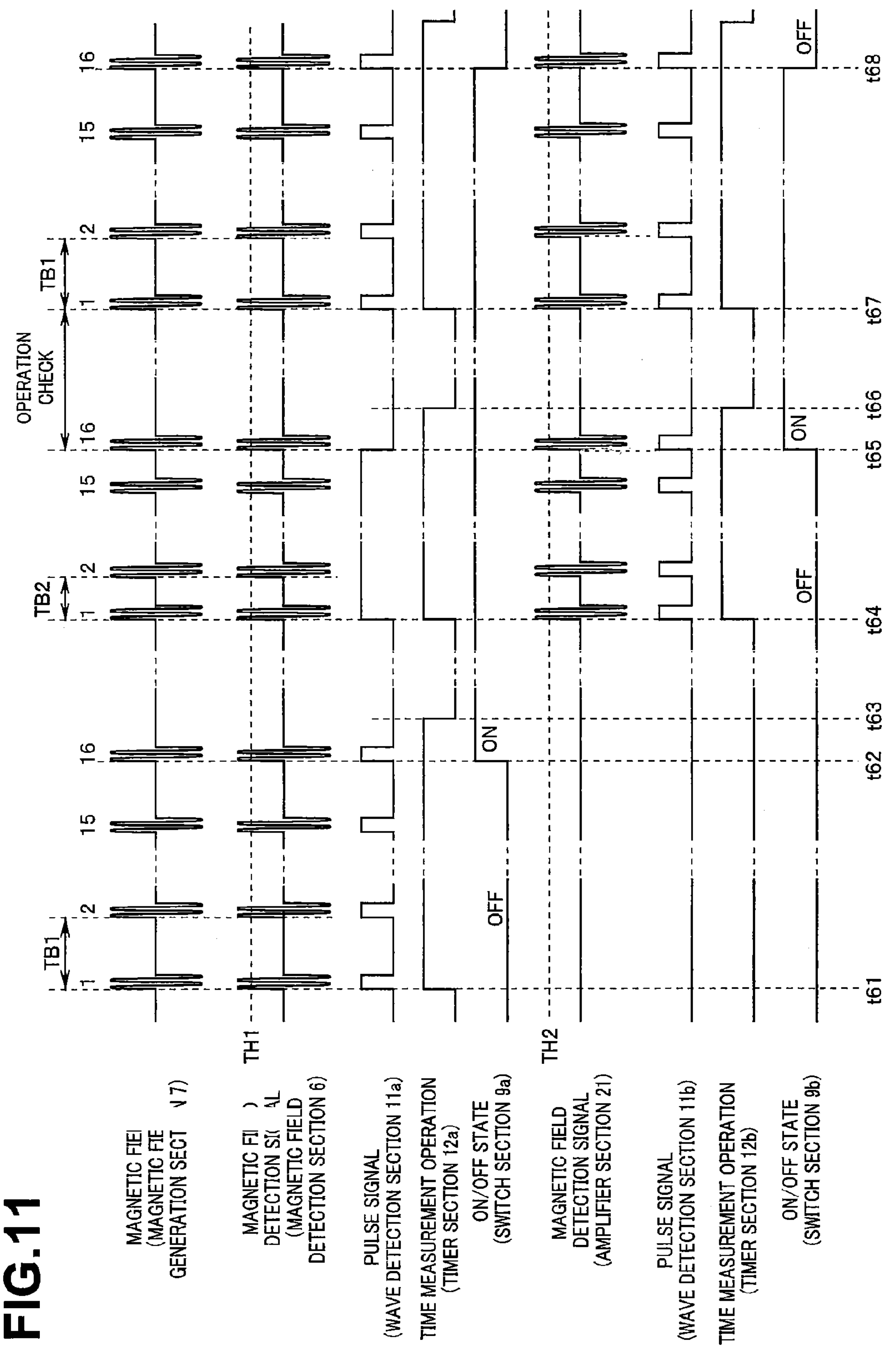
FIG. 11 illustrates a timing chart for describing an example, which is different from the example shown in FIG. 10, of the operation of the biological information acquiring apparatus according to the second embodiment.

FIGS. 10 and 11 relate to the second embodiment of the present invention.

Note that, in the present embodiment, detailed description of the parts having the same configurations and the like as those in the first embodiment will be omitted, and the parts having configurations and the like different from those in the first embodiment will be mainly described.

The present embodiment is applicable to a biological information acquiring system 101 having substantially the same configurations as those in the first embodiment. However, the present embodiment is different from the first embodiment in that the capacities of the capacitors CB and CC and the resistance values of the resistors RB and RC are respectively set such that the time constant $\tau 1$ of the wave detection section 11*a* is larger than the time constant $\tau 2$ of the wave detection section 11*b*.

In addition, in the present embodiment, the signal output counting value PA of the counter section 13*a* and the signal output counting value PB of the counter section 13*b* are set to the same value.

Furthermore, the magnetic field generation section 7 according to the present embodiment is provided with a fourth and a fifth magnetic field generation switches, instead of the first, second, third magnetic field generation switches.

Note that the above-described time constants $\tau 1$ and $\tau 2$ may be set to arbitrary values, respectively, as long as these values have a magnitude relationship of $\tau 1 > \tau 2$.

Now detailed description will be made on the case where the biological information acquiring apparatus 1 is arranged in the body cavity of the subject, with reference to the timing chart in FIG. 10, as needed. FIG. 10 illustrates the timing chart for describing one example of an operation of the biological information acquiring apparatus according to the second embodiment.

Note that, in the description related to the timing chart in FIG. 10, description will be made, for simplification, supposing that each of the latch sections 14*a* and 14*b* is configured by a D flip-flop and operates in synchronization with rising of signals. In addition, in the description related to the timing chart in FIG. 10, description will be made, for simplification, by taking a case where the values of the above-described signal output counting values PA and PB are 16, and the time constant $\tau 2$ is half of the time constant $\tau 1$, as an example.

First, in an initial state corresponding to the period before a time t51, since no alternate-current magnetic field is generated from the magnetic field generation section 7, both of the switch sections 9*a* and 9*b* are in the off state. In addition, in the initial state like this, power is supplied from the power source section 8 to the signal reception section 10*a*, whereas power is not supplied from the power source section 8 to each of the illumination section 2, the image pickup section 3, the radio transmission section 4, and the signal reception section 10*b*. In addition, in the above-described initial state, the operation of each of the illumination section 2, the image pickup section 3, the radio transmission section 4, and the signal reception section 10*b* completely stops, and the signal reception section 10*a* hardly operates, since no alternate-current magnetic field is generated from the magnetic field generation section 7. Therefore, in the above-described initial state, input-standby state of the magnetic field detection signal from the magnetic field detection section 6 is maintained, with the consumption of the power supplied from the power source section 8 limited to the minimum.

Then, when the fourth magnetic field generation switch (not shown) provided on the magnetic field generation section 7 is turned on by the operator or the like at the time t51, for example, the first generation of the burst alternate-current magnetic field, out of the total 16 times of generations of the burst alternate-current magnetic field each of which is performed once in a cycle TB1 coincident with the time constant $\tau 1$, is performed by the magnetic field generation section 7.

In addition, when the first generation, out of the total 16 times of generations, of the burst alternate-current magnetic field is performed by the magnetic field generation section 7 at the time t51, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. Furthermore, in accordance with such operations performed at the time t51, the counting value of the counter section 13*a* is updated to 1.

After that, at a time t52, when the 16th generation, out of the total 16 times of generations, of the burst alternate-current magnetic field is performed by the magnetic field generation section 7, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t52, the counting value of the counter section 13*a* is updated to 16, the output signal outputted from the counter section 13*a* is inputted to the latch section 14*a*, the switching signal outputted from the latch section 14*a* is inverted, and the switch section 9*a* is switched from OFF to ON.

Therefore, according to the above-described operations of the respective sections, when the time reaches the time t52, the switch section 9*a* is turned on, thereby starting the supply of the power from the power source section 8 to the signal reception section 10*b*.

Note that, since the power is not supplied to the signal reception section 10*b* before the time t52, even if the magnetic field detection signal from the magnetic field detection section 6 is inputted to (the amplifier section 21 of) the signal reception section 10*b*, the switching signal is not outputted from the latch section 14*b* and the switch section 9*b* is maintained in the off state.

On the other hand, the timer section 12*a* operates such that the counting value of the counter section 13*a* is reset to zero, when completing the time measurement operation for measuring the certain time period TA1 at a time t53 after the time t52. In other words, in the case where the counting value of the counter section 13*a* does not reach 16 before the certain time period TA1 corresponding to the period from the time t51 to the time t53 elapses, the counting value of the counter section 13*a* is reset to zero, and thereby the switching signal outputted from the latch section 14*a* is maintained without being inverted. As a result, since the switch section 9*a* is not switched from OFF to ON, supply of the power from the power source section 8 to the signal reception section 10*b* is not started.

Subsequently, the subject swallows the biological information acquiring apparatus 1 at a time t54 after the t53, and thereby the biological information acquiring apparatus 1 is arranged in the body cavity of the subject.

After that, when the fifth magnetic field generation switch (not shown) provided on the magnetic field generation section 7 is turned on by the operator or the like at a time t55, for example, the first generation of the burst alternate-current magnetic field, out of the total 16 times of generations of the burst alternate-current magnetic field each of which is performed once in a cycle TB2 coincident with the time constant τ2, is performed by the magnetic field generation section 7.

In addition, when the first generation, out of the total 16 times of generations, of the burst alternate-current magnetic field is performed by the magnetic field generation section 7 at the time t55, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t55, the counting value of the counter section 13*b* is updated to 1.

After that, when the 16th generation, out of the total 16 times of generations, of the burst alternate-current magnetic field is performed by the magnetic field generation section 7 at a time t56, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t56, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from OFF to ON.

Therefore, according to the above-described operations of the respective sections, when the time reaches the time t56, the switch section 9*b* is turned on, thereby starting the supply of the power from the power source section 8 to the illumination section 2, the image pickup section 3 and the radio transmission section 4, that is, resulting in a transition to a state where the image data in the body cavity of the subject can be acquired.

Note that, after the time t55, since the biological information acquiring apparatus 1 is arranged in the body cavity of the subject, the signal level of the magnetic field detection signal outputted from the magnetic field detection section 6 becomes smaller than the threshold TH1 which can be detected in the wave detection section 11*a*. In addition, in the wave detection section 11*a* whose time constant is set to τ1, it is impossible to detect waves in synchronization with the output interval of the magnetic field detection signal outputted from the magnetic field detection section 6 for each cycle TB2 which is half of the cycle TB1. Therefore, even if the magnetic field detection signal from the magnetic field detection section 6 is inputted to (the wave detection section 11*a* of) the signal reception section 10*a* after the time t55 while the biological information acquiring apparatus 1 is arranged in the body cavity of the subject, the switching signal outputted from the latch section 14*a* is not inverted, and the switch section 9*a* is maintained in the on state.

On the other hand, the timer section 12*b* operates such that the counting value of the counter section 13*b* is reset to zero, when completing the time measurement operation for measuring the certain time period TA2 at a time t57 after the time t56. In other words, in the case where the counting value of the counter section 13*b* does not reach 16 before the certain time period TA2 corresponding to the period from the time t55 to time t57 elapses, the counting value of the counter section 13*b* is reset to zero, and thereby the switching signal outputted from the latch section 14*b* is maintained without being inverted. As a result, since the switch section 9*b* is not switched from OFF to ON, the supply of the power from the power source section 8 to each of the illumination section 2, the image pickup section 3 and the radio transmission section 4 is not started.

After that, when the fifth magnetic field generation switch (not shown) provided on the magnetic field generation section 7 is turned on again by the operator or the like at a time t58, for example, the first generation of the burst alternate-current magnetic field, out of the total 16 times of generations of the burst alternate-current magnetic field each of which is performed once in a cycle TB2 coincident with the time constant τ2, is performed by the magnetic field generation section 7.

In addition, when the first generation, out of the total 16 times of generations, of the burst alternate-current magnetic field is performed by the magnetic field generation section 7 at the time t58, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t58, the counting value of the counter section 13*b* is updated to 1.

After that, when the 16th generation, out of the total 16 times of generations, of the burst alternate-current magnetic field is performed by the magnetic field generation section 7 at a time t59, the magnetic field detection signal having the signal level below the threshold TH1 is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*. Furthermore, in accordance with such operations performed at the time t59, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from ON to OFF.

Therefore, according to the above-described operations of the respective sections, when the time reaches the time t59, the switch section 9*b* is switched from ON to OFF, thereby stopping the supply of the power from the power source section 8 to each of the illumination section 2, the image pickup section 3 and the radio transmission section 4, that is, resulting in a transition from the state where the image date inside the body cavity of the subject can be acquired to the state where the image data inside the body cavity of the subject cannot be acquired.

Furthermore, according to the above-described operations from the time t58 to the time t59, for example, the image data acquired after the time t57 is displayed on the monitor or the like, not shown, and confirmed, thereby capable of stopping the supply of the power to each of the illumination section 2, the image pickup section 3, and the radio transmission section 4 once in such a case that it is found out that the biological information acquiring apparatus 1 has not reached a desired region to be observed.

On the other hand, the timer section 12*b* operates such that the counting value of the counter section 13*b* is reset to zero, when completing the time measurement operation for measuring the certain time period TA2 at a time t60 after the time t59. In other words, in the case where the counting value of the counter section 13*b* does not reach 16 before the certain time period TA2 corresponding to the period from the time t58 to the time t60 elapses, the counting value of the counter section 13*b* is reset to zero, and thereby the switching signal outputted from the latch section 14*b* is maintained without being inverted. As a result, since the switch section 9*b* is not switched from ON to OFF, supply of the power from the power source section 8 to each of the illumination section 2, the image pickup section 3, and the radio transmission section 4 is continued.

Next, detailed description will be made on the case where operation check is performed before the biological information acquiring apparatus 1 is arranged in the body cavity of the subject, with reference to the timing chart in FIG. 11, as needed. FIG. 11 illustrates a timing chart for describing an example, which is different from the example shown in FIG. 10, of the operation of the biological information acquiring apparatus according to the second embodiment.

Note that, in the description related to the timing chart in FIG. 11, description will be made, for simplification, supposing that each of the latch sections 14*a* and 14*b* is configured by a D flip-flop and operates in synchronization with rising of signals. In addition, in the description related to the timing chart in FIG. 11, description will be made, for simplification, by taking the case where the values of the above-described signal output counting values PA and PB are 16, and the time constant τ2 is half of the time constant τ1, as an example. Furthermore, in the description related to the timing chart in FIG. 11, description will be made, for simplification, by taking the above-described case where TA1 is equal to TA2 as an example.

First, in an initial state corresponding to the period before the time t61, since no alternate-current magnetic field is generated from the magnetic field generation section 7, both of the switch section 9*a* and the switch section 9*b* are in the off state. Then, in the initial state like this, power is supplied from the power source section 8 to the signal reception section 10*a*, whereas power is not supplied from the power source section 8 to each of the illumination section 2, the image pickup section 3, the radio transmission section 4 and the signal reception section 10*b*.

Then, when the fourth magnetic field generation switch (not shown) provided on the magnetic field generation section 7 is turned on by the operator or the like at the time t61, for example, the first generation of the burst alternate-current magnetic field, out of the total 16 times of generations of the burst alternate-current magnetic field each of which is performed once in the cycle TB1 coincident with the time constant τ1, is performed by the magnetic field generation section 7.

In addition, when the first generation, out of the total 16 times of generations, of the burst alternate-current magnetic field is performed by the magnetic field generation section 7 at the time t61, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. Furthermore, in accordance with such operations performed at the time t61, the counting value of the counter section 13*a* is updated to 1.

After that, when the 16th generation, out of the total 16 times of generations, of the burst alternate-current magnetic field is performed by the magnetic field generation section 7 at a time t62, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t62, the counting value of the counter section 13*a* is updated to 16, the output signal outputted from the counter section 13*a* is inputted to the latch section 14*a*, the switching signal outputted from the latch section 14*a* is inverted, and the switch section 9*a* is switched from OFF to ON.

Therefore, according to the above-described operations of the respective sections, when the time reaches the time t62, the switch section 9*a* is turned on, thereby starting the supply of the power from the power source section 8 to the signal reception section 10*b*.

Note that, since power is not supplied to the signal reception section 10*b* before the time t62, even if the magnetic field detection signal from the magnetic field detection section 6 is inputted to (the amplifier section 21 of) the signal reception section 10*b*, the switching signal is not outputted from the latch section 14*b* and the switch section 9*b* is maintained in the off state.

On the other hand, the timer section 12*a* operates such that the counting value of the counter section 13*a* is reset to zero, when completing the time measurement operation for measuring the certain time period TA1 at the time t62 after the time t63. In other words, in the case where the counting value of the counter section 13*a* does not reach 16 before the certain time period TA1 corresponding to the period from the time t61 to the time t63 elapses, the counting value of the counter section 13*a* is reset to zero, and thereby the switching signal outputted from the latch section 14*a* is maintained without being inverted. As a result, since the switch section 9*a* is not switched OFF to ON, supply of the power from the power source section 8 to the signal reception section 10*b* is not started.

Subsequently, when the fifth magnetic field generation switch (not shown) provided on the magnetic field generation section 7 is turned on by the operator or the like at a time t64 after the time t63, for example, the first generation of the burst alternate-current magnetic field, out of the total 16 times of generations of the burst alternate-current magnetic field each of which is performed once in the cycle TB2 coincident with the time constant τ2, is performed by the magnetic field generation section 7.

In addition, when the first generation, out of the total 16 times of generations, of the burst alternate-current magnetic field is performed by the magnetic field generation section 7 at the time t64, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t64, the counting value of the counter section 13*b* is updated to 1.

After that, when the 16th generation, out of 16 times of generations, of the burst alternate-current magnetic field is performed by the magnetic field generation section 7 at a time t65, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, and the pulse signal acquired by detecting the magnetic field detection signal from the amplifier section 21 is outputted from the wave detection section 11*b* to the counter section 13*b*. Furthermore, in accordance with such operations performed at the time t65, the counting value of the counter section 13*b* is updated to 16, the output signal outputted from the counter section 13*b* is inputted to the latch section 14*b*, the switching signal outputted from the latch section 14*b* is inverted, and the switch section 9*b* is switched from OFF to ON.

Therefore, according to the above-described operations of the respective sections, when the time reaches the time t65, the switch section 9*b* is turned on, thereby starting the supply of the power from the power source section 8 to each of the illumination section 2, the image pickup section 3, and the radio transmission section 4, that is, resulting in a transition to a state where the operation check of the biological information acquiring apparatus 1 is possible.

On the other hand, the timer section 12*a* operates such that the counting value of the counter section 13*a* is reset to zero, when completing the time measurement operation for measuring the certain time period TA1 at a time t66 after the time t65. In addition, the timer section 12*b* operates such that the counting value of the counter section 13*b* is reset to zero, when completing the time measurement operation for measuring the certain time period TA2 at the time t66 after the time t65.

After the time t64, since the biological information acquiring apparatus 1 has not been arranged in the body cavity of the subject yet, the signal level of the magnetic field detection signal outputted from the magnetic field detection section 6 is equal to or higher than the threshold TH1 which can be detected by the wave detection section 11*a*. However, in the wave detection section 11*a* whose time constant is set to τ1, it is impossible to detect waves in synchronization with the output interval of the magnetic field detection signal outputted from the magnetic field detection section 6 for each cycle TB2 which is half of the cycle TB1. Then, according to such an operation of the wave detection section 11*a*, even if the certain time period TA1 corresponding to the period from the time t64 to the time t66 elapses, the counting value of the counter section 13*a* does not reach 16. Therefore, the switching signal outputted from the latch section 14*a* is not inverted even after the time t66, that is, the switch section 9*a* is maintained in the on state even after the time t66.

Subsequently, when the fourth magnetic field generation switch (not shown) provided on the magnetic field generation section 7 is turned on again by the operator or the like at a time t67 after the completion of the operation check of the biological information acquiring apparatus 1, for example, the first generation of the burst alternate-current magnetic field, out of the total 16 times of generations of the burst alternate-current magnetic field each of which is performed once in the cycle TB1 coincident with the time constant τ1, is performed by the magnetic field generation section 7.

Then, when the first generation, out of the total 16 times of generations, of the burst alternate-current magnetic field is performed by the magnetic field generation section 7 at the time t67, the magnetic field detection signal having the signal level of the threshold TH1 or above is outputted from the magnetic field detection section 6, the pulse signal acquired by detecting the magnetic field detection signal from the magnetic field detection section 6 is outputted from the wave detection section 11*a* to the counter section 13*a*, and the time measurement operation for measuring the certain time period TA1 is started in the timer section 12*a*. In addition, when the first generation, out of the total 16th generations, of the burst alternate-current magnetic field is performed by the magnetic field generation section 7 at the time t67, the magnetic field detection signal having the signal level of the threshold TH1 or above is outputted from the magnetic field detection section 6, the magnetic field detection signal amplified so as to have the signal level of the threshold TH2 or above is outputted from the amplifier section 21 to the wave detection section 11*b*, the pulse signal acquired by detecting the magnetic field detection signal from the amplifier section 21 is outputted from the wave detection section 11*b* to the counter section 13*b*, and the time measurement operation for measuring the certain time period TA2 is started in the timer section 12*b*. Furthermore, in accordance with such operations performed at the time t67, the counting values of the counter section 13*a* and the counter section 13*b* are respectively updated to 1.

After that, when the 16th generation, out of the total 16 times of generations, of the burst alternate-current magnetic field is performed by the magnetic field generation section 7 at the time t68, the magnetic field detection signal having the signal level of the threshold TH1 or above is outputted from the magnetic field detection section 6, and the pulse signal acquired by detecting the magnetic field detection signal from the magnetic field detection section 6 is outputted from the wave detection section 11*a* to the counter section 13*a*. Furthermore, in accordance with such operations performed at the time t68, the counting value of the counter section 13*a* is updated to 16, the output signal outputted from the counter section 13*a* is inputted to the latch section 14*a*, the switching signal outputted from the latch section 14*a* is inverted, and the switch section 9*a* is switched from ON to OFF.

On the other hand, at the time t68, the switch section 9*a* is switched from ON to OFF, thereby stopping the supply of the power to the signal reception section 10*b* and the switching signal is not outputted from the latch section 14*b*. As a result, also the switch section 9*b* is switched from ON to OFF.

Therefore, the operator or the like performs operation check of the biological information acquiring apparatus 1 before arranging the biological information acquiring apparatus in the body cavity of the subject, and thereafter operates the fourth magnetic field generation switch provided on the magnetic field generation section 7, thereby capable of bringing the power source state of the biological information acquiring apparatus 1 from the high power consumption state in which each of the illumination section 2, the image pickup section 3 and the radio transmission section 4 is activated to the low power consumption state corresponding to the input standby state of the magnetic field detection signal from the magnetic field detection section 6 all at once.

Note that, according to the present embodiment, in addition to the above-described fourth and fifth magnetic field generation switches, a sixth magnetic field generation switch (not shown) for continuously generating the burst alternate-current magnetic field generated once for the each cycle TB1, 16 times in total, and the burst alternate-current magnetic field generated once for the each cycle TB2, 16 times in total may be provided on the magnetic field generation section 7, for example.

Furthermore, the configuration described in the first embodiment and the configuration described in the present embodiment may be combined appropriately.

Note that, the present embodiment shows an example in which the fourth magnetic field generation switch, the fifth magnetic field generation switch, and the sixth magnetic field generation switch (all not shown) are provided on the magnetic field generation section 7, and the burst alternate-current magnetic fields having the cycles in accordance with the respective switches are generated. However, the present embodiment is not limited to such a configuration. Specifically, coils which respectively generate burst alternate-current magnetic fields having different cycles may be integrally configured or a part of or all of the coils may be configured as separate bodies, for example. Furthermore, apparatuses which respectively generate burst magnetic fields having different cycles may be integrally configured (such as the magnetic field generation section 7), or a part of or all of the apparatuses may be configured as separate bodies, for example.

As described above, the present embodiment provides the configuration which enables control for changing the power source state of the biological information acquiring apparatus based on the combination of the threshold of the signal level at which the magnetic field detection signal acquired by detecting the alternate-current magnetic field generated in a burst form can be detected and the time constant for determining availability of the wave detection in synchronous with the output interval of the magnetic field detection signal. Therefore, according to the present embodiment, it is possible to switch ON and OFF of the power source of the biological information acquiring apparatus more surely than in conventional apparatuses, without increasing the size of the antenna incorporated into the biological information acquiring apparatus, for example.

Figure 12:
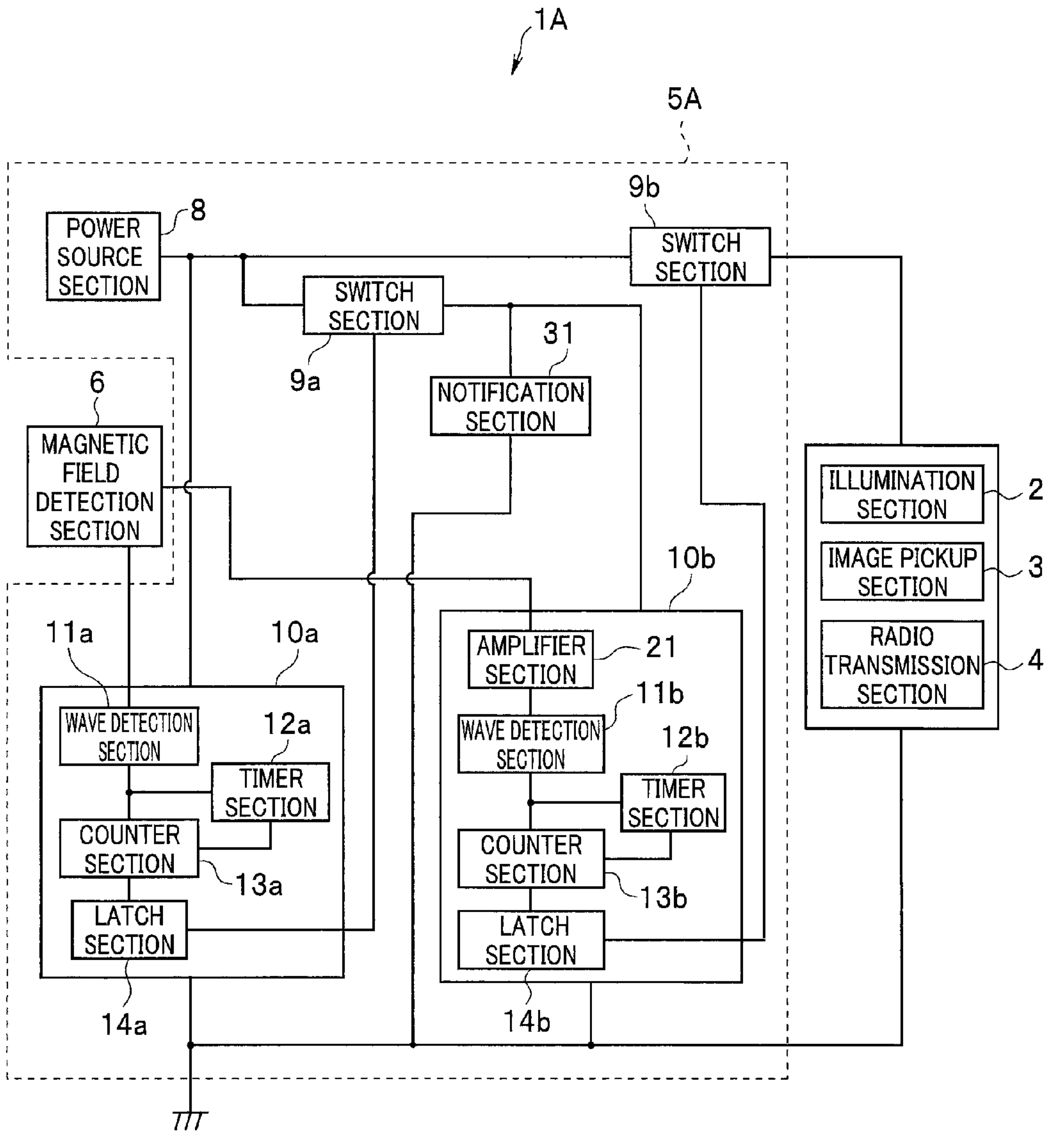
FIG. 12 illustrates an example of a configuration in which a notification section is added to the biological information acquiring apparatus in FIG. 2.

Incidentally, in the above-described first and second embodiments, the biological information acquiring apparatus may be configured as a biological information acquiring apparatus 1A provided with a power supplying section 5A configured by adding a notification section 31 to the above-described power supplying section 5, as shown in FIG. 12, for example. FIG. 12 illustrates an example of a configuration in which a notification section is added to the biological information acquiring apparatus in FIG. 2.

The notification section 31 of the power supplying section 5A is connected such that power is supplied from the power source section 8 when the switch section 9*a* is turned on, and power supply from the power source section 8 is stopped when the switch section 9*a* is turned off, as shown in FIG. 12.

In addition, the notification section 31 is configured by including a light-emitting element such as an LED in which a light-emission surface which emits light when the switch section 9*a* is turned on is arranged so as to face the outer surface of the biological information acquiring apparatus 1A, or a radio signal transmission circuit capable of generating a notification signal which is transmitted outside the biological information acquiring apparatus 1A by radio when the switch section 9*a* is turned on. Note that the notification section 31 may have a configuration different from the above-described one, as long as the notification section has a configuration which is capable of notifying the operator or the like that the switch section 9*a* has been turned on.

In this configuration, when the notification section 31 is configured by including the light-emitting element, the notification section 31 emits light when the switch section 9*a* is in the on state. In addition, when the notification section 31 is configured by including the light-emitting element, the light emission of the notification section 31 is stopped when the switch section 9*a* is in the off state.

Therefore, when the notification section 31 is configured by including the light-emitting element, the operator or the like can easily confirm whether or not the switch section 9*a* is in the on state by visually confirming the light-emission state of the notification section 31. As a result, the operator or the like can arrange the biological information acquiring apparatus 1A in the body cavity of the subject with the switch section 9*a* being surely turned on, for example.

Note that, when the notification section 31 is configured by including the light-emitting element, it is possible to save the power consumption of the power source section 8 as much as possible by reducing the light amount of the light-emitting element in a visually recognizable range for the operator, for example.

On the other hand, when the notification section 31 is configured by including the radio signal transmission circuit, radio transmission of a notification signal indicating that the switch section 9*a* is in the on state is started at the timing when the switch section 9*a* is switched from OFF to ON. In addition, when the notification section 31 is configured by including the radio signal transmission circuit, the radio transmission of the notification signal indicating that the switch section 9*a* is in the on state is stopped at the timing when the switch section 9*a* is switched from ON to OFF.

In addition, when the notification section 31 is configured by including the radio signal transmission circuit, it is possible to display on a display device (not shown) an image or a character string or the like indicating that the switch section 9*a* is in the on state by receiving a notification signal transmitted from the radio signal transmission circuit by radio and performing various signal processings on the notification signal.

Therefore, when the notification section 31 is configured by including the radio signal transmission circuit, the operator or the like can easily confirm whether or not the switch section 9*a* is in the on state by visually confirming the image or the character string or the like displayed on the display device (not shown) in response to the radio transmission of the notification signal from the radio signal transmission circuit. As a result, the operator or the like can arrange the biological information acquiring apparatus 1A in the body cavity of the subject with the switch section 9*a* being surely turned on, for example.

Note that the biological information acquiring apparatus 1A as described above is not limited to the one in which the notification section 31 is additionally provided, but may include the function of the above-described notification section 31 in either the illumination section 2 or the radio transmission section 4, for example. In addition, the function of the notification section 31 is included into the illumination section 2, the light-emission state such as a light-emitting interval of the illumination section 2 may be different between the case where the switch section 9*a* is in the on state and the switch 9*b* is in the off state, and the case where both of the switch section 9*a* and the switch section 9*b* are in the on state, for example.

Figure 13:
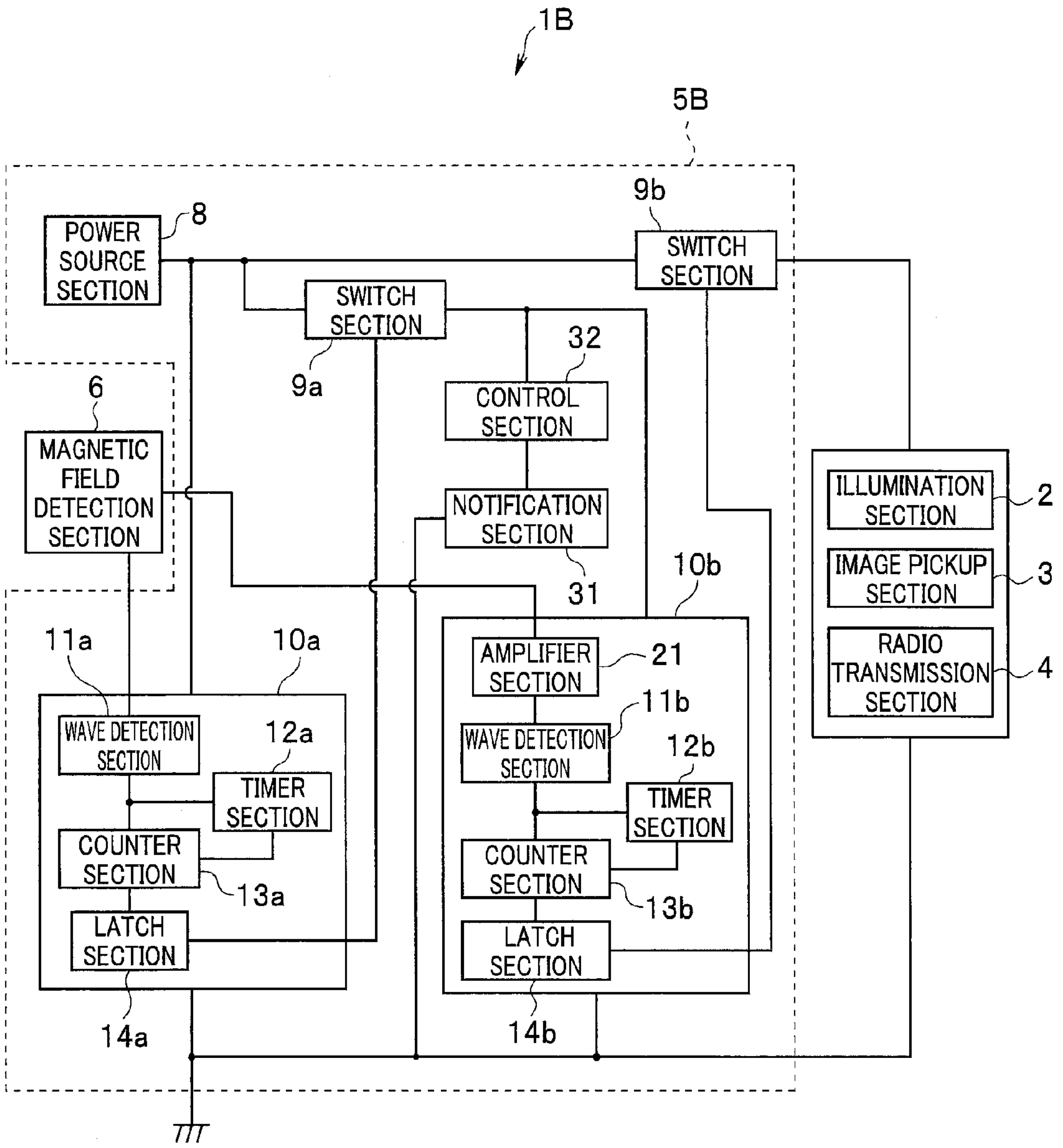
FIG. 13 illustrates an example of a configuration in which a notification section and a control section are added to the biological information acquiring apparatus in FIG. 2.

In addition, in the above-described first and second embodiments, the biological information acquiring section may be configured as a biological information acquiring apparatus 1B including a power supplying section 5B configured by adding the notification section 31 and a control section 32 to the above-described power supplying section 5, as shown in FIG. 13, for example. FIG. 13 illustrates an example of a configuration in which the notification section and a control section are added to the biological information acquiring apparatus in FIG. 2.

The notification section 31 of the power supplying section 5B has substantially the same configuration and function as those in the notification section 31 of the power supplying section 5A.

The control section 32 of the power supplying section 5B is connected in series between the output side of the switch section 9*a* and the input side of the notification section 31, as shown in FIG. 13. Therefore, when the switch section 9*a* is turned on, power is supplied from the power source section 8 to both of the control section 32 and the notification section 31, and when the switch section 9*a* is turned off, the power supply to both of the control section 32 and the notification section 31 is stopped.

In addition, the control section 32 of the power supplying section 5B is configured so as to be able to output a control signal for causing the notification section 31 to operate intermittently when the switch section 9*a* is in the on state. Therefore, when the notification section 31 is configured by including the light-emitting element, for example, the light-emitting element blinks in response to the control signal from the control section 32. On the other hand, when the notification section 31 is configured by including the radio signal transmission circuit, for example, the notification signal having a waveform according to the control signal from the control section 32 is transmitted by radio.

In this configuration, when the notification section 31 is configured by including the light-emitting element, the notification section 31 blinks when the switch section 9*a* is in the on state. In addition, when the notification section 31 is configured by including the light-emitting element, the light emission of the notification section 31 is stopped when the switch section 9*a* is in the off state.

Therefore, when the notification section 31 is configured by including the light-emitting element, the operator or the like can easily confirm whether or not the switch section 9*a* is in the on state by visually confirming the blinking state of the notification section 31. As a result, the operator or the like can arrange the biological information acquiring apparatus 1B in the body cavity of the subject with the switch section 9*a* being surely turned on, for example.

Note that, when the notification section 31 is configured by including the light-emitting element, it is possible to save the power consumption of the power source section 8 as much as possible by reducing the light amount of the light-emitting element in a visually recognizable range for the operator, for example.

On the other hand, when the notification section 31 is configured by including the radio signal transmission circuit, for example, the radio transmission of the notification signal indicating that the switch section 9*a* is in the on state is started at the timing when the switch section 9*a* is switched from OFF to ON. In addition, when the notification section 31 is configured by including the radio signal transmission circuit, the radio transmission of the notification signal indicating that the switch section 9*a* is in the on state is stopped at the timing when the switch section 9*a* is switched from ON to OFF.

Furthermore, when the notification section 31 is configured by including the radio signal transmission circuit, it is possible to display on a display device (not shown) an image or a character string or the like indicating that the switch section 9*a* is in the on state by receiving a notification signal transmitted from the radio signal transmission circuit by radio and performing various signal processings on the notification signal.

Therefore, when the notification section 31 is configured by including the radio signal transmission circuit, the operator or the like can easily confirm whether or not the switch section 9*a* is in the on state by visually confirming the image or the character string or the like displayed on the display device (not shown) in response to the radio transmission of the notification signal from the radio signal transmission circuit. As a result, the operator or the like can arrange the biological information acquiring apparatus 1B in the body cavity of the subject with the switch section 9*a* being surely turned on, for example.

That is, according to the biological information acquiring apparatus 1B having the above-described power supplying section 5B, it is possible to acquire substantially the same working and effects as those of the biological information acquiring apparatus 1A having the power supplying section 5A, and it is also possible to further reduce the power consumption required when notifying that the switch section 9*a* is in the on state, compared with the biological information acquiring apparatus 1A having the power supplying section 5A.

Figure 14:
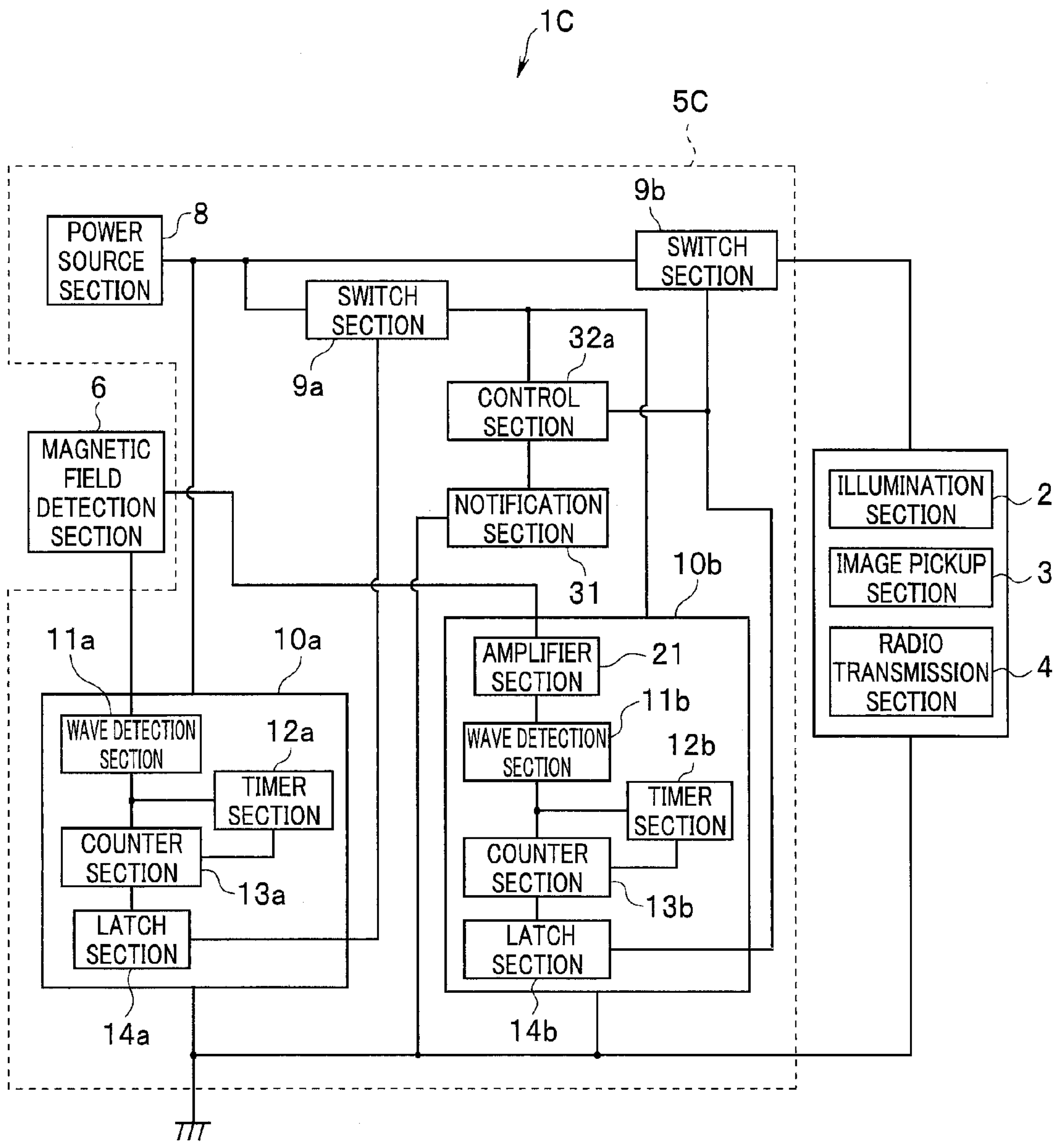
FIG. 14 illustrates an example, which is different from the example shown in FIG. 13, of the configuration in which a notification section and a control section are added to the biological information acquiring apparatus in FIG. 2.

In addition, in the above-described first and second embodiments, the biological information acquiring apparatus may be configured as a biological information acquiring apparatus 1C having a power supplying section 5C configured by adding a notification section 31 and a control section 32*a* to the above-described power supplying section 5, as shown in FIG. 14, for example. FIG. 14 illustrates an example, which is different from the example shown in FIG. 13, of the configuration in which the notification section and the control section are added to the biological information acquiring apparatus in FIG. 2.

The notification section 31 of the power supplying section 5C has substantially the same configuration and function as those of the notification section 31 of the power supplying section 5A.

The control section 32*a* of the power supplying section 5C is connected in series between the output side of the switch section 9*a* and the input side of the notification section 31, as shown in FIG. 14. Therefore, when the switch section 9*a* is turned on, power is supplied from the power source section 8 to both of the control section 32*a* and the notification section 31, and when the switch section 9*a* is turned off, the power supply to both of the control section 32*a* and the notification section 31 is stopped.

In addition, the control section 32*a* of the power supplying section 5C is configured to detect the on state or the off state of the switch section 9*b* based on the output state of the switching signal from the latch section 14*b* of the signal reception section 10*b*, when the switch section 9*a* is in the on state, and configured, based on the detection result, to be able to output to the notification section 31*a* control signal for bringing the notification section 31 into an opposite operation state with respect to the on state or off state of the switching section 9*b*. Therefore, the control section 32*a* outputs a control signal for causing the notification section 31 to operate when detecting that the switch section 9*b* is in the off state based on the output state of the switching signal from the latch section 14*b* of the signal reception section 10*b*, for example. In addition, the control section 32*a* outputs a control signal for stopping the operation of the notification section 31 when detecting that the switch section 9*b* is in the on state based on the output state of the switching signal from the latch section 14*b* of the signal reception section 10*b*, for example.

Note that the control section 32*a* may be configured by including substantially the same function as that of the control section 32 in the power supplying section 5B. Specifically, the control section 32*a* may be configured to output a control signal for causing the notification section 31 to operate intermittently when detecting that the switch section 9*b* is in the off state.

According to the biological information acquiring apparatus 1C including the above-described power supplying section 5C, the notification section 31 operates (or operates intermittently) when the switch section 9*a* is in the on state and the switch section 9*b* is in the off state. In addition, according to the biological information acquiring apparatus 1C including the above-described power supplying section 5C, the operation of the notification section 31 is stopped when both of the switch sections 9*a* and 9*b* are in the on state.

When the notification section 31 is configured by including the light-emitting element, the notification section 31 emits light (or blinks) when the switch section 9*a* is in the on state and the switch 9*b* is in the off state. In addition, when the notification section 31 is configured by including the light-emitting element, the light emission of the notification section 31 is stopped when the switch section 9*a* is in the off state. Furthermore, when the notification section 31 is configured by including the light-emitting element, the light emission of the notification section 31 is stopped when both of the switch sections 9*a* and 9*b* are in the on state.

Therefore, when the notification section 31 is configured by including the light-emitting element, the operator or the like can easily confirm that the switch section 9*a* is in the on state with the switch section 9*b* being in the off state by visually confirming the light-emission (or blinking) state of the notification section 31. As a result, the operator or the like can arrange the biological information acquiring apparatus 1C into the body cavity of the subject with the switch section 9*b* being turned off and the switch section 9*a* being surely turned on, for example.

Note that when the notification section 31 is configured by including the light-emitting element, it is possible to save the power consumption of the power source section 8 as much as possible by reducing the light amount of the light-emitting element in a visually recognizable range for the operator, for example.

On the other hand, when the notification section 31 is configured by including the radio signal transmission circuit, the radio transmission of a notification signal indicating that only the switch section 9*a* is in the on state is started at the timing when the switch section 9*a* is switched from OFF to ON and the timing when the switch section 9*b* is switched from ON to OFF. In addition, when the notification section 31 is configured by including the radio signal transmission circuit, the radio transmission of the notification signal indicating that only the switch section 9*a* is in the on state is stopped at the timing when the switch section 9*a* is switched from ON to OFF and at the timing when the switch section 9*b* is switched from OFF to ON.

Furthermore, when the notification section 31 is configured by including the radio signal transmission circuit, it is possible to display on the display device (not shown) an image or a character string or the like indicating that the switch section 9*a* is in the on state with the switch section 9*b* is being in the off state by receiving the notification signal transmitted from the radio signal transmission circuit by radio and performing various signal processings on the received notification signal.

Therefore, when the notification section 31 is configured by including the radio signal transmission circuit, the operator or the like can easily confirm that the switch section 9*a* is in the on state with the switch section 9*b* being in the off state by visually confirming the image or the character string or the like displayed on the display device (not shown) in response to the radio transmission of the notification signal from the radio signal transmission circuit. As a result, the operator or the like can arrange the biological information acquiring apparatus 1C in the body cavity of the subject with the switch section 9*b* being in the off state and the switch section 9*a* being surely in the on state, for example.

That is, according to the biological information acquiring apparatus 1C having the above-described power supplying section 5C, it is possible to acquire substantially the same working and effects as those of the biological information acquiring apparatus 1A having the power supplying section 5A, and it is also possible to further reduce the power consumption required when notifying that the switch section 9*a* is in the on state, compared with the biological information acquiring apparatus 1A having the power supplying section 5A.

In addition, according to the biological information acquiring apparatus 1C having the above-described power supplying section 5C, when the notification section 31 is configured by including the light-emitting element, the light-emission of the light-emitting element is stopped when the switch section 9*b* is turned on, for example. Therefore, when the notification section 31 of the above-described power supplying section 5C is configured by including the light-emitting element, it is possible to prevent the reflection of the light-emitting element which is likely to occur when image data is acquired by the image pickup section 3.

Note that the function of the power supplying section 5B of the biological information acquiring apparatus 1B can be incorporated into the power supplying section 5C of the biological information acquiring apparatus 1C. According to the biological information acquiring apparatus 1C having the power supplying section 5C configured by incorporating the function of the power supplying section 5B, it is possible to further reduce the power consumption required when notifying that the switch section 9*a* is in the on state, compared with the biological information acquiring apparatus 1B having the power supplying section 5B.

Note that the present invention is not limited to the above-described embodiments, and it is needless to say that various changes and modifications are possible without departing from the gist of the invention.

What is claimed is:

1. A biological information acquiring system comprising: a biological information acquiring apparatus including a biological information acquiring section that is configured to acquire biological information inside a subject; and a magnetic field generation section configured to be able to generate a burst alternate-current magnetic field, the biological information acquiring apparatus includes:

a power source section that is configured to supply power for driving the biological information acquiring section;

a magnetic field detection section which generates a magnetic field detection signal according to a detection result of the burst alternate-current magnetic field generated from the magnetic field generation section and outputs the generated magnetic field detection signal;

a first switching control section which performs control so as to switch between an on state and an off state of a first switch section connected to the power source section or maintain the on state or the off state of the first switch section, based on an output state of the magnetic field detection signal; and a second switching control section which performs control so as to switch between an on state and an off state of a second switch section connected between the power source section and the biological information acquiring section or maintain the on state or the off state of the second switch section, based on the output state of the magnetic field detection signal, when power is supplied from the power source section by the first switch section being turned on.

2. The biological information acquiring system according to claim 1, wherein the first switching control section performs control so as to switch between the on state and the off state of the first switch section and is configured to detect that a number of times of output of the magnetic field detection signal outputted from the magnetic field detection section for each predetermined output interval reaches a first threshold, and the second switching control section performs control so as to switch between the on state and the off state of the second switch section and is configured to detect that the number of times of output of the magnetic field detection signal outputted from the magnetic field detection section for the each predetermined output interval reaches a second threshold which is smaller than the first threshold.

3. The biological information acquiring system according to claim 1, wherein the first switching control section performs control so as to switch between the on state and the off state of the first switch section and is configured to detect that the magnetic field detection signal outputted from the magnetic field detection section for each output interval which is equal to or longer than a first output interval is outputted for a predetermined number of times, and the second switch control section performs control so as to switch between the on state and the off state of the second switch section, and is configured to detect that the magnetic field detection signal outputted from the magnetic field detection section for each output interval which is equal to or longer than a second output interval shorter than the first output interval is outputted for the predetermined number of times.

4. The biological information acquiring system according to claim 1, wherein the first switching control section performs control so as to maintain the on state or the off state of the first switch section when a signal level of the magnetic field detection signal is lower than a predetermined value.

5. The biological information acquiring system according to claim 1, further comprising a notification section that is configured to notify whether or not the first switch section is in the on state.

6. The biological information acquiring system according to claim 5, wherein the notification section includes a light-emitting element that is configured to notify whether or not the first switch section is in the on state by emitting light or stopping light emission according to the on state or the off state of the first switch section.

7. The biological information acquiring system according to claim 5, wherein the notification section includes a radio signal transmission circuit that is configured to transmit by radio a notification signal for causing information indicating the on state or the off state of the first switch section to be displayed on a display device.

8. The biological information acquiring system according to claim 1, wherein the biological information acquiring section includes an illumination section which emits illumination light for illuminating an object inside the subject and an image pickup section that picks up an image of the subject illuminated by the illumination section and acquires image data, and the illumination section includes a function configured to notify whether or not the first switch section is in the on state by emitting light or stopping light emission according to the on state or the off state of the first switch section.

9. The biological information acquiring system according to claim 1, wherein the biological information acquiring apparatus is a capsule endoscope.

10. A method of driving the biological information acquiring system according to claim 1, the method comprising:

a step in which power supply from the power source section to the second switching control section is started by a control performed by the first switching control section when a burst alternate-current magnetic field generated once for each predetermined cycle is generated from the magnetic field generation section by a first number of times; and a step in which, in a case where power is supplied from the power source section to the second switching control section, power supply state from the power source section to the biological information acquiring section is switched by a control performed by the second switching control section, every time the burst alternate-current magnetic field generated once for the each predetermined cycle is generated from the magnetic field generation section by a second number of times which is smaller than the first number of times.

11. A method of driving the biological information acquiring system according to claim 1, the method comprising:

a step in which power supply from the power source section to the second switching control section is started by a control performed by the first switching control section when a burst alternate-current magnetic field generated once for each first cycle is generated from the magnetic field generation section by a predetermined number of times; and a step in which, in a case where power is supplied from the power source section to the second switching control section, power supply state from the power source section to the biological information acquiring section is switched by a control performed by the second switching control section, every time the burst alternate-current magnetic field generated once for each second cycle which is shorter than the first cycle is generated from the magnetic field generation section by the predetermined number of times.

* * * * *